US010568954B2

(12) United States Patent
Witvliet et al.

(10) Patent No.: US 10,568,954 B2
(45) Date of Patent: Feb. 25, 2020

(54) PROCESS FOR READY-TO-USE PCV/M.HYO COMBINATION VACCINE

(71) Applicant: Intervet Inc., Madison, NJ (US)

(72) Inventors: Maarten Hendrik Witvliet, Oostrum (NL); Theodorus Jansen, Venray (NL); Huchappa Gowda Jayappa, Trophy Club, TX (US)

(73) Assignee: Intervet Inc., Madison, NJ (US)

( * ) Notice: Subject to any disclaimer, the term of this patent is extended or adjusted under 35 U.S.C. 154(b) by 139 days.

(21) Appl. No.: 15/534,232

(22) PCT Filed: Dec. 10, 2015

(86) PCT No.: PCT/EP2015/079212
§ 371 (c)(1),
(2) Date: Jun. 8, 2017

(87) PCT Pub. No.: WO2016/091998
PCT Pub. Date: Jun. 16, 2016

(65) Prior Publication Data
US 2017/0340723 A1 Nov. 30, 2017

(30) Foreign Application Priority Data
Dec. 11, 2014 (EP) ..................................... 14197477

(51) Int. Cl.
*A61K 39/12* (2006.01)
*A61K 39/02* (2006.01)
*C07K 14/30* (2006.01)
*A61K 39/00* (2006.01)

(52) U.S. Cl.
CPC .......... *A61K 39/12* (2013.01); *A61K 39/0241* (2013.01); *C07K 14/30* (2013.01); *A61K 2039/552* (2013.01); *A61K 2039/55505* (2013.01); *A61K 2039/55511* (2013.01); *A61K 2039/70* (2013.01); *C12N 2750/10034* (2013.01)

(58) Field of Classification Search
None
See application file for complete search history.

(56) References Cited

U.S. PATENT DOCUMENTS

2013/0266603 A1  10/2013  Nitzel

FOREIGN PATENT DOCUMENTS

| WO | 1993016726 A2 | 9/1993 |
| WO | 2007028823 A1 | 3/2007 |
| WO | 2009126356 A2 | 10/2009 |
| WO | 2013/152083 A2 | 10/2013 |
| WO | 2014182872 A1 | 11/2014 |

OTHER PUBLICATIONS

Al-Shakhshir et al, Effect of protein adsorption on the, Vaccines, 1994, pp. 472-474, vol. 12, Issue 5.
Astrup, P. and K.V. Larsen, Safety of Porcilis PCV in pure breed Danish pigs, Proceedings 21st IPVS congress, p. 049, Vancouver Jul. 18-21, 2010.
Boehringer Ingelheim, Boehringer Ingelheim Animal Health sees freshly mixed swine vaccines as its way forward, Boehringer Ingelheim website, 2014, http://www.boehringer-ingelheim.com/news/news_releases/press_releases/2014/01_september_2014animal.html.
Eggen et al., "Combining mycoplasma hyopneumoniae and Porcine Circovirus Type 2, a research report"; Proceedings of the 5th Asian Pig Veterinary Society Congress, Mar. 7-9, 2011; p. 109. CAS-XP055258982.
Eggen, A.A. et al., One-dose vaccination against Mycoplasma hyopneumoniae and porcine circovirus type 2, Proceedings of the 21st IPVS congress, 2010, p. 110, Vancouver, Jul. 18-21.
European Search Report for 14197477.4 dated Jul. 22, 2015, 8 pages.
Farreres et al., Serology and saety of the simultaneous use of Porcilis PCV and M+PAC in the field, Proceedings of the 21st IPVS congress, 2010, p. 408.
Farreres, J et al, Safety and efficacy of the simultaneous administration of Porcilis PCV and Porcilis MHyo under field conditions, Porcine Circovirus Associated Diseases (PCVAD), Jul. 18, 2010, pp. 409.
Gillespie, J. et al., Porcine circovirus type 2 and porcine circovirus-associated disease, J Vet Intern Med, 2009, pp. 1151-1163, 23.
Hem, S.L. and Hogenesch. H., Relationship between physical and chemical properties of aluminum-containing adjuvants and immunopotentiation, www.future-drugs.com Expert Rev. Vaccines, 2007, pp. 685-698, 6(5).
Interantional Search report, dated Mar. 29, 2016, Interantional Search report for PCTEP/2015/079212 dated Mar. 29, 2016, 5 pages.
Kim, D. et al., Comparative efficacy of commercial Mycoplasma hyopneumoniae and porcine circovirus 2 (PCV2) vaccines in pigs experimentally infected with M. hyopneumoniae and PCV2, Vaccine, 2011, pp. 3206-3212, 29.
M + PAC. "Summary of Product Characteristics M+ PAC". Registration file / Dec. 2010; pp. 1-2; XP055258988; Retrieved from the Internet: URL:http://fs-1.5mpublishing.com/images/MSD/PDF/SPC-MPac.pdf. May 3, 2012.

(Continued)

Primary Examiner — Brian Gangle

(57) ABSTRACT

The present invention describes a process for the preparation of an antigen composition, which antigen composition can be used to prepare a ready-to-use vaccine for swine, for preventing or reducing infection by M. hyo or PCV2 and associated signs of disease. The process is characterised in that it comprises a step of admixing a PCV2 antigen to a pre-formed antigen/adjuvant complex of an M. hyo antigen adsorbed to an Aluminium-hydroxide adjuvant. This way a PCV2/M. hyo combination vaccine can be prepared that is highly effective already after a single administration, against infection and disease by M. hyo and PCV2 either when in single or in combined infections. Also the vaccine has very good safety upon administration, is ready-to-use, and is economically feasible.

20 Claims, 4 Drawing Sheets

(56) References Cited

OTHER PUBLICATIONS

Figure 1:
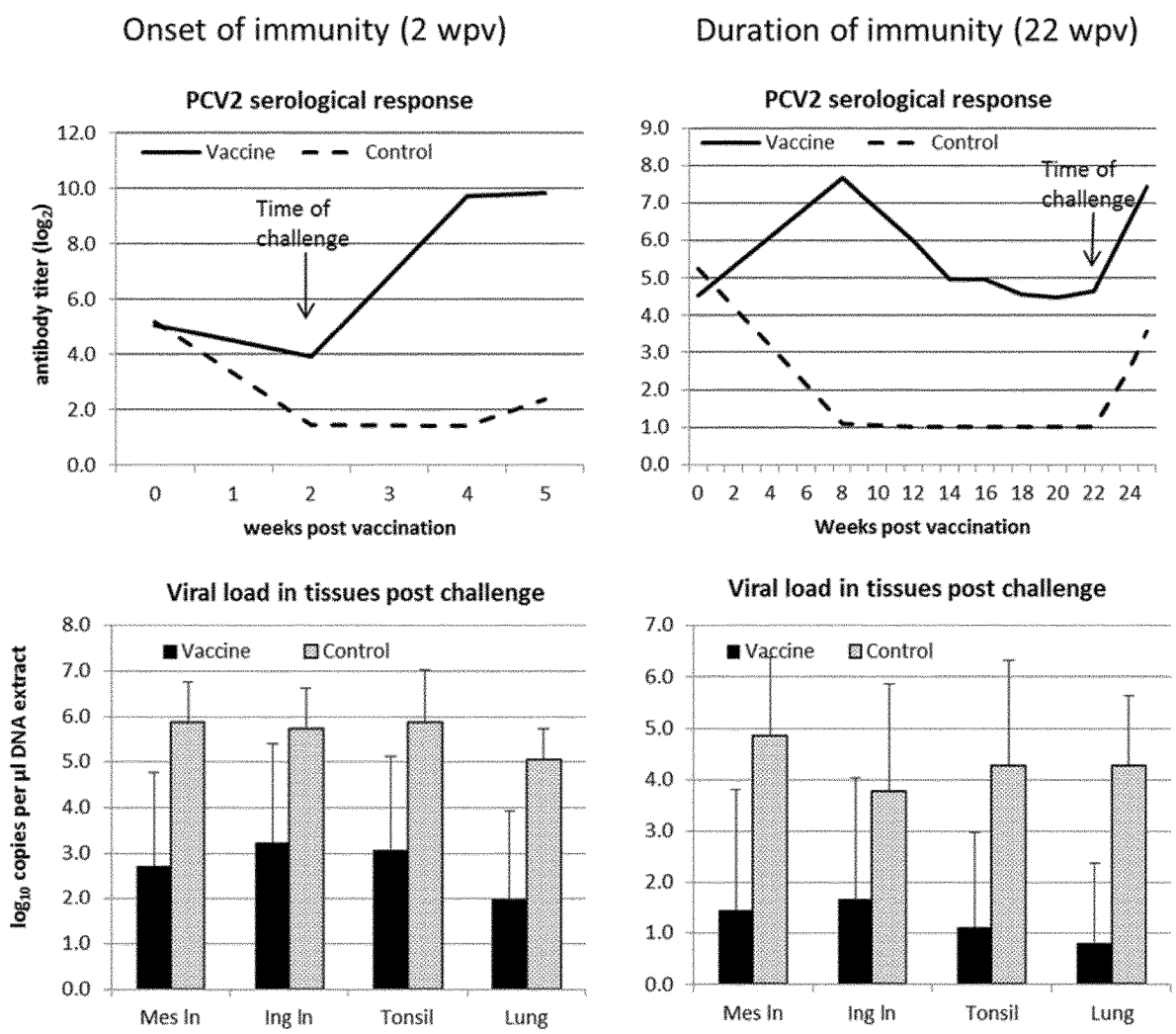

Msd Animal Health, "M+PAC, Fewer Lesions, More Growth" Brochure, CAS-XP055194733; Jul. 18, 2010; pp. 1-10. Retrieved from the Internet:http://fs-1.5mpublishing.com/images/MSD/PDF/M_PAC.pdf.

Palacios, J et al, Economic evaluation of a combined vaccination against PCV-2 and Mh on a commercial farm, Porcine Circovirus Associated Diseases (PCVAD)—Control, Jul. 18-21, 2010, pp. 387.

Ruiz et al., Clinical and pathologic lesions after simultaneous vaccination with PCV2 and Mycoplasma vaccine in 3 week old piglets, Porcine Circovirus Associated Diseases, Jul. 21, 2010, p. 438; CAS-XP055259199.

Seo, H.W. et al, Interaction of porcine circovirus type 2 and Mycoplasma hyopneumoniae vaccines on dually infected pigs, Vaccine, 2014, pp. 2480-2486, vol. 32.

PROCESS FOR READY-TO-USE PCV/M.HYO COMBINATION VACCINE

CROSS-REFERENCE TO RELATED APPLICATIONS

This application is a national stage entry under 35 U.S.C. § 371 of PCT/EP2015/079212 filed on Dec. 10, 2015, which claims priority to EP 14197477.4, filed on Dec. 11, 2014. The content of PCT/EP2015/079212 is hereby incorporated by reference in its entirety.

The present invention relates to the field of veterinary medicine, namely to vaccines for swine against *Mycoplasma hyopneumoniae* and against porcine circovirus type 2. In particular the invention relates to a new process for preparing a composition containing the vaccine antigens. This composition then allows the production of effective ready-to-use combination vaccines for swine. Further the invention relates to the use of the antigen composition obtainable by the new process, to a vaccine prepared from that antigen composition, and to various methods and uses of the antigen composition and the vaccine.

*Mycoplasma hyopneumoniae* (*M. hyo*) is the primary agent causing (porcine) enzootic pneumonia (EP), a chronic respiratory disease in swine, occurring worldwide. In earlier literature an objective synonym was used: *M. suipneumoniae*, referring to the same bacterium. The bacterium is relatively small, lacks a cell wall, and belongs to the class of Mollicutes. Especially young piglets are vulnerable to this highly contagious disease, and transmission is usually airborne or by direct contact.

Pulmonary disease from *M. hyo* is largely an immune-mediated pathology leading to consolidated pneumonia. Although not excreting prominent toxins, the bacterium colonizes and damages the pulmonary ciliated epithelium, leading to loss of ciliary activity. Dependent on housing conditions and environmental stress, the most problematic consequence of this disease is that it predisposes for different secondary infections of the porcine respiratory system, by other bacterial- and viral pathogens. This gives rise to the so called: Porcine Respiratory Disease Complex (PRDC), displaying severe lung lesions. Next to discomfort to the animal, EP and PRDC cause important economic losses to the swine industry due to reduced performance in growth rate and feed conversion ratio, as well as through costs for veterinary care and antibiotics use (Thacker & Minion, 2012, Mycoplasmosis, in: Disease of swine, 10th ed., J. Wiley & Sons, p. 779-797).

Other swine pathogens relevant to PRDC are: viruses such as: porcine circovirus type 2, swine Influenza virus, and porcine reproductive respiratory syndrome virus; and bacteria such as: *Haemophilus parasuis*, *Pasteurella multocida*, *Streptococcus suis* and *Actinobacillus pleuropneumoniae*.

As antibiotics are only partially effective, the main treatment against *M. hyo*-related disease and production losses, is by vaccination, preferably early in life. For a review, see: Maes et al. (2008, Vet. Microbiol., vol. 126, p. 297-309). Commonly piglets are vaccinated in the nursery, up to 4 weeks old, optionally with booster vaccinations some weeks later.

The exact mechanism of disease control by vaccine-induced immunity against *M. hyo* is not fully understood. Although vaccination cannot completely prevent pulmonary colonisation or bacterial transmission, vaccination is nevertheless effective in substantially reducing clinical signs such as lung colonisation, lung lesions, and pneumonia, in reducing shedding, and in restoring economic performance, such as average daily weight gain. To monitor vaccine efficacy, different clinical disease parameters can be scored and monitored such as morbidity, pneumonia, pleuritis, but also by detection or quantification of re-isolated *M. hyo*, such as by serology, histology, or PCR.

A common way to determine the efficacy and protection of an *M. hyo* vaccine is by scoring a reduction in severity of lung lesions. Such lesions are typically scored during necropsy by macroscopic assessment of lung consolidation, for example as based on the Goodwin scale (Goodwin et al., 1969, J. Hyg. Camb., vol. 67, p. 465-476), this scale runs from zero up to a maximum of 55 points for totally affected lungs. With effective vaccines, reductions of over 50% in lung lesion scores can be observed when comparing the effect of challenge infection in vaccinated versus unvaccinated animals. Such a reduction in lung lesion score is indicative for effective immune protection, and correlates to significantly restoring swine health as well as swine performance as measured in feed conversion ratio and average daily weight gain (Maes et al., 2008, Vet. Microbiol., vol. 126, p. 297-309).

*M. hyo* can be cultured in vitro, but requires a very rich culture-medium to compensate for its small genome that lacks the capability to convert essential nutrients itself. An example is the medium described by Friis (1975, Nord Vet. Med., vol. 27, p. 337-339), which is a complicated medium that contains yeast extract, animal serum and various extracts of porcine and bovine origin. When fully grown, the complete *M. hyo* culture is usually inactivated by chemical or physical means, e.g. using formalin, to produce a 'bacterin' type antigen: killed whole cell-culture antigens of *M. hyo*. Subsequently the inactivated culture can be concentrated (e.g. 10-20 times), e.g. by filtration and used for the formulation of a vaccine. Resulting from the use of rich media and the concentration, such *M. hyo* bacterin antigens contain many medium-derived proteins, fatty acids, etc., which may influence the further processing into a vaccine.

Many commercial vaccines against *M. hyo* exist and these are routinely used in the majority of commercial swine farming operations. Generally these are inactivated vaccines prepared from adjuvated bacterins which are administered by parenteral injection. Some examples are: RespiSure™ (Zoetis), Ingelvac™ *M. hyo*, and MycoFLEX™ (Boehringer Ingelheim), Hyoresp™ (Merial), Stellamune™ Mycoplasma (Elanco Animal Health), and M+Pac™ (Merck Animal Health).

Well-known strains of *M. hyo* that are used in vaccine production or -development are: J strain (ATCC deposit nr. 25934), strain 11, or strain 232.

Several variations and refinements have been made to these vaccines, e.g. in the type of adjuvant used (mineral oil, non-mineral oil, aluminium salts, synthetic polymers, etc.), the dose to be applied (1 or 2 ml), the age of vaccination (1 day, 7 days or older, 3 weeks, 6 weeks or older, etc.), or the administration route (intramuscular, subcutaneous, or intradermal).

The M+Pac vaccine comprises a dual adjuvant, Emunade™ which is an oil-in-water emulsion of a mineral oil dispersed in a watery carrier, whereby the watery carrier contains an Aluminium-hydroxide adjuvant. The M+Pac vaccine has been commercially available since 1996.

A recent development in *M. hyo* vaccines are adaptations to the dosing regimen, by providing vaccines that do not require a booster vaccination, so-called: 'one-shot' or 'single shot' vaccines. Alternatively, vaccines of which the dosing is flexible were developed: either a one-shot or a dual dose, this is a so-called: 'flex-dose', for instance as 2 times 1 ml, or as once 2 ml.

Next to oil-based emulsion adjuvants, aluminium salts have been used as adjuvant for *M. hyo* vaccines. Aluminium salts are well known adjuvants, and for human vaccines they are the main type of adjuvant. Different salts are being used: 'Aluminium-hydroxide adjuvant', which is crystalline aluminium oxyhydroxide (AlO(OH)); 'Aluminium-phosphate adjuvant', which is amorphous aluminium hydroxyphosphate $Al(OH)_m(PO_4)_n$; and 'Aluminium-sulphate adjuvant', or: 'Alum', which is amorphous aluminium hydroxysulphate $(AlK(SO_4)_2)$. The last two types are derivatives of aluminium oxyhydroxide, by the replacement of hydroxyl groups by phosphate-respectively sulphate-groups. For a review see: Hem & HogenEsch (2007, Expert Rev. Vaccines, vol. 6, p. 685-698).

The mechanism of action of aluminium-salt adjuvants is still not completely understood; at the basis is the adsorption of antigens to the aluminium salt, and their release inside the body of the vaccinated target. The binding of antigens to an aluminium salt is a result of different types of associations, such as physical entrapment, but also electrostatic interactions between oppositely charged molecules. In addition covalent bonds can be created through anionic ligand exchange whereby phosphate groups from the antigen substitute for hydroxyl groups on the aluminium salt. Through these different types of association the antigen and the aluminium salt adjuvant form a complex wherein the bound antigen may have a modified structure, but can also be stabilised.

Inside the target's body the adjuvant-antigen complex is degraded by the conditions and enzymes in the interstitial fluid, and the antigen becomes dissociated and is available for the immune system. Thereby the aluminium salt stimulates the uptake of antigen by antigen-presenting cells. Also, aluminium salts induce a strong Th2 response, and thus the production of antibodies (Exley et al. 2010, Trends in Immunol., vol. 31, p. 103-109).

In the Aluminium-hydroxide adjuvant, the aluminium salt is in the form of a boehmite crystal. This gives the salt a fibrous structure which in water forms an aqueous colloidal gel. This is also the way the product is available commercially, for example as: Alhydrogel™ (Brenntag Biosector), Rehydragel™ (Reheis), and Rehsorptar™ (Armour Pharmaceutical). These products are available in different concentrations and qualities, and may also differ in the size of the crystals; smaller crystals have more antigen binding capacity. The Aluminium-hydroxide adjuvant has a point-of-zero-charge of about 11, meaning that at a pH below 11, it is positively charged. Consequently, at a physiological pH between 6 and 8, the adjuvant can adsorb negatively charged antigenic proteins (Al-Shakshir et al., 1994, Vaccine, vol. 12, p. 472-474).

Adsorption and complex formation initiates rapidly, but complete adsorption can take several hours. Adsorption levels also depend on the binding capacity of the aluminium salt used. To quantify its protein binding capacity, a binding assay using a known amount of a standard protein can be used; for the Aluminium-hydroxide adjuvant a standard binding assay is prescribed in European Pharmacopoeia monograph 1664. Commercial Aluminium-hydroxide adjuvant commonly can bind up to 2.5 mg of albumin per mg of Aluminium at physiological pH.

Another very relevant pathogen of swine that has large economic impact is porcine circovirus type 2 (PCV2). For a review see Gillespie et al. (2009, J. Vet. Intern. Med., vol. 23, p. 1151-1163). PCV2 was originally identified as the causative agent of the "postweaning multisystemic wasting syndrome" (PMWS), observed in young swine. The clinical signs and pathology include progressive wasting, dyspnea, tachypnea, and occasionally icterus and jaundice. Porcine circovirus belongs to the family of Circoviridae, and has a small (17 nm) icosahedral non-enveloped virus, with a capsid containing a circular, single stranded DNA genome of about 1760 nucleotides. The genome contains only a few open reading frames, of which ORF2 encodes the viral capsid protein of about 28 kDa. This contains the main virus-neutralising epitopes.

PCV2 is relatively stable, and highly infectious. It is shed via different kinds of body-secretions, and spreads both horizontally and vertically in a swine herd. As PCV2 is lymphotropic, the main lesions caused by PCV2 infection are lymphoid depletions. This causes immunosuppression so that an animal infected with PCV2 becomes susceptible to secondary infections. Consequently, next to PMWS, PCV2 is also involved in a number of other swine disease syndromes which are collectively named: porcine circovirus (associated) disease (PCVD, or PCVAD). The most pronounced PCVDs are Porcine Respiratory Disease Complex, Porcine Dermatitis and Nephropathy Syndrome, reproductive failure, granulomatous enteritis, congenital tremors, and exudative epidermitis.

Without overt signs of a secondary infection however, the majority of PCV2 infected swine do not show clear clinical symptoms of disease. Such subclinical infections with PCV2 only manifest themselves by poor growth and -performance in apparently healthy swine.

(Sub-)Clinical symptoms of PCVD caused by PCV2 can be observed in swine usually from 3 or 4 weeks of age onwards, which is the time at which the piglets are weaned and protective maternally derived antibodies start to decline.

To protect against PCV2, commercial vaccines have been developed, and these are being used worldwide. Different types of vaccine are: a vaccine based on inactivated whole PCV2 virus (Circovac™ Merial), or inactivated chimeric PCV1/PCV2 virus (Suvaxyn™ PCV/Fostera™ PCV, Zoetis); or a subunit vaccine based on recombinant expressed Capsid protein (Ingelvac™ CircoFLEX, Boehringer Ingelheim; Porcilis™ PCV/Circumvent™ PCV, Merck/MSD AH). This last type of vaccine is produced by the recombinant expression of the PCV2 ORF2 in a baculovirus/insect cell expression system. The expressed capsids self-assemble into a virus-like particle (VLP). This resembles a native PCV2 virion, except that it lacks the viral genome, and therefore is non-replicative. Vaccines based on such PCV2 VLPs have demonstrated to be safe and effective, already at about 20 microgram PCV2 VLP per animal dose, adjuvated as an oil-in-water emulsion (see: WO 07/028.823).

Depending on the type of adjuvant used, PCV2 vaccine efficacy can be based more on humoral- or on cellular immunity. Titres can be measured e.g. using a commercial Elisa: Synbiotics SERELISA™ PCV2 Ab Mono Blocking ELISA. Alternatively an in-house indirect Elisa can be used, as described by Haake et al. (2014, Vet. Microbial., vol. 168, p. 272-280)

PCV2 vaccines reduce PCV2 viral replication and -spread. This reduces PCV2 viral load in lungs and lymphoid tissues, and protects against lymphoid depletion, PCVD, and horizontal spread of infections. Consequently this restores general health and performance in vaccinated swine herds such as by: reduced mortality, better average daily weight gain and improved feed conversion.

Vaccine efficacy and protection can be measured by determining PCV2 specific antibody levels, or by detection of the PCV2 viral load in serum or in secretions (oral, nasal, faecal, urinary), or by detecting other pathogens involved in PCVD, via PCR, (immuno-)histology, hybridisation, or serologically.

PCV2 strains used for vaccine development are commonly of the PCV2a genotype; these also cross-protect against strains of the PCV2b genotype.

Oil-adjuvanted vaccines against PCV2 such as Porcilis PCV, have been reported to induce moderate to severe local reactions at the injection site. See e.g. Astrup & Larsen (2010, Poster no. P.049, in: Proceedings 21$^{st}$ IPVS Congress, Canada, 18-21 July). For several days after inoculation, local swelling was observed up to several centimetres in size. However these injection site reactions are painless and transient and therefore within acceptable limits. In addition they did not correlate to consistent systemic reactions, and were of no effect to vaccination efficacy. Nevertheless, there is room for improvement of the safety of this type of vaccines.

Disease symptoms from PCV2 infection can be exacerbated by infection with M. hyo, and vice versa. Therefore for effective protection of swine, vaccination against both PCV2 and M. hyo is required to maintain good swine health and economic profitability. Dual vaccination can therefore be applied using separate single-antigen vaccines against PCV2 and against M. hyo. However for ease of administration, and to save labour costs a combined vaccine is preferred. In addition, young swine are very sensitive to environmental stressors, therefore reducing the number of times they are handled is directly beneficial to their health and performance. Even better is when the combination vaccine does not require a booster vaccination, so that a single administration protects against multiple diseases during the whole of the fattening period.

Commercial combination vaccines against PCV2 and M. hyo are available that allow vaccination against both pathogens in one administration, see Kim et al. (2011, Vaccine, vol. 29, p. 3206-3212). Examples are: Circumvent™ PCV-M (MSD AH) and Fostera™ PCV MH (Zoetis), both are ready-to-use combination vaccines for flex-dose administration, and are oil-in-water emulsions with oily adjuvants. In product leaflets on Fostera PCV MH, Zoetis describe that they have overcome interference between the M. hyo and the PCV antigens, by applying purification of the M. hyo antigen by Protein A column-chromatography, before combination with PCV2 antigen. However, the skilled person will understand that such elaborate purification is laborious and expensive, and reduces the economic feasibility of the vaccine product.

Related is also Ingelvac™ CircoFLEX/MycoFLEX™ (Boehringer Ingelheim), which employs an aqueous polymer adjuvant. However this last vaccine is not ready-to-use and requires the field-side mixing of two vaccine components from separate bottles, shortly before administration, which is impractical.

So, although all these vaccines are effective, further adaptations and improvements in regard of safety, efficacy, or ease of use would bring increased benefit to the veterinary field.

An experimental PCV2/M. hyo vaccine in Emunade adjuvant has been described previously (Eggen et al., 2010, Oral presentation no. O.072, in: Proceedings 21$^{st}$ IPVS Congress, Canada, 18-21 July). This vaccine demonstrated fairly good reduction of M. hyo induced lung lesions (NB: with n=8, and corrected for outliers), and induced levels of anti-PCV2 antibodies considered efficacious for this type of vaccine. The vaccine had been prepared by admixing M. hyo and PCV2 antigens with an empty Emunade oil-in water emulsion. The authors conclude that in principle PCV2 and M. hyo antigens can be combined into a ready-to-use vaccine, without immunological interference in the target.

However this vaccine was not suited for large scale commercialisation, because the PCV2 VLP antigen that was used had been purified to more than 90% purity by ultracentrifugation over a CsCl-gradient. This was done to in an attempt to increase the safety and prevent local site-reactions. Because this type of downstream processing of antigens is very labour-intensive and extremely expensive, it is not economically feasible for application a large scale, especially not in the highly cost-aware field of veterinary vaccines.

Recently published International patent application WO 2014/182872 describes a ready-to-use PCV2/M. hyo combination vaccine. This vaccine is prepared by first solubilising M. hyo antigen, then mixing this with saponin; next solubilising PCV2 antigen, and adding that to the M. hyo/saponin mixture. Finally the mixture of solubilised antigens is combined either with an oil-adjuvant or with an aluminium adjuvant. None of the examples describes the preparation or use of an aluminium adjuvanted vaccine.

A recent publication further demonstrates that the development of a ready-to-use PCV2/M. hyo combination vaccine is still very difficult: Boehringer Ingelheim, who produce and market the Ingelvac™ CircoFLEX/MycoFLEX™ vaccine for field-side mixing, have recently released a press-statement indicating they have terminated their efforts to develop a ready-to-use PCV2/M. hyo combination vaccine. This because of their failure to achieve acceptable levels of safety and efficacy. The Boehringer Ingelheim, corporate press release of 1 Sep. 2014 (www.boehringer-ingelheim.com/news/news_releases/press_releases/2014/01_september_2014animal.html) states:

"Boehringer Ingelheim Animal Health, a market-leading manufacturer of swine vaccines, has decided to remain focused on freshly mixed Porcine Circovirus type 2 (PCV2)/Mycoplasma hyopneumoniae (M. hyo) vaccines and not follow the development of a PCV2/M. hyo ready-to-use (RTU) vaccine combination. As a consequence, the company has discontinued its PCV2/M. hyo RTU research program. Although initial data was promising, it became evident over time that in this case, the RTU design does not meet the high standards of efficacy and safety for which Boehringer Ingelheim's FLEXcombo® platform is known."

Consequently, there is a continued need in the field for an improved combination vaccine against M. hyo and PCV2, which is effective and safe, is user-friendly, and is economically feasible.

It is therefore an object of the present invention to overcome disadvantages in the prior art, and to accommodate to this need in the field by providing a PCV2/M. hyo combination vaccine that is highly effective against infection and disease caused by PCV2 and by M. hyo, already as a single shot vaccine, that has very good safety upon administration, and that is ready-to-use.

Initially the inventors were disappointed to learn that the results as published by Eggen et al. (supra) could not be obtained when using a standard PCV2 VLP antigen. Such a standard antigen is what is used in commercial PCV2 VLP vaccines such as Porcilis PCV/Circumvent PCV vaccines. It has acceptable safety and is highly effective. However rather than being highly purified, it is produced with a more economically feasible level of downstream processing. This way the antigen is much less pure.

Following the procedure applied by Eggen et al., the inventors made a straightforward combination of an M. hyo bacterin and such a standard PCV2 VLP antigen with empty Emunade adjuvant. Unfortunately a vaccine was obtained that provided less than half the normal level of protection against an M. hyo challenge infection: lung lesions were only reduced by 30%, as compared to reduction by 66% when using a vaccine with only M. hyo antigen in Emunade (M+Pac™). Results are presented in the Examples section hereinafter.

The inventors were therefore surprised to find that the M. hyo vaccine efficacy in a ready-to-use PCV2/M. hyo combination vaccine for swine could only be brought to desired levels, by applying a special process to the preparation of the composition containing the vaccine antigens: by adding PCV2 antigen only after the complex of M. hyo antigen and Aluminium-hydroxide adjuvant had been formed.

Similarly, the inventors were surprised to find that a PCV2/M. hyo combination vaccine as described herein demonstrated such a significantly improved safety profile as compared to a PCV2 single-antigen vaccine.

The PCV2/M. hyo combination vaccine that can be made from this specially prepared antigen composition, is highly effective against infection and disease by M. hyo and PCV2 already after a single administration, has very good safety upon administration, is ready-to-use, and is economically feasible in that it can accommodate a PCV2 antigen which is not highly pure. In fact, the vaccine's efficacy equals the efficacy of single-antigen vaccines against M. hyo or PCV2. Also the safety upon administration is complete in that no significant vaccine-induced local- or systemic reactions were observed upon its use in swine.

In view of the potentially large scale at which such a combination vaccine may be used in the swine producing industry, these effects and improvements are significant, and represent a surprising technical effect that has great commercial significance. Therefore, in this way the object of the invention can be met, and consequently disadvantages of the prior art can be overcome.

It is currently not known why a PCV2 antigen must not be present while the M. hyo antigen adsorbs to the Aluminium-hydroxide adjuvant. Nor is it known why the safety of the new PCV2/M. hyo combination vaccine is so good.

Although the inventors do not want to be bound by any theory or model that might explain these observations, they speculate that when a PCV2 antigen is present during the formation of the complex between M. hyo antigen and the Aluminium-hydroxide adjuvant, this may interfere in some way or form with the efficient adsorption of an M. hyo antigen to Aluminium-hydroxide adjuvant. Also, the PCV2 antigen, which does not bind to the Aluminium hydroxide adjuvant as does the M. hyo antigen, may become entangled into the forming complex. In one way or other this interferes with the later immune-response against the M. hyo antigen.

Similarly speculative is the cause of the increased safety of the new combination vaccine. This may have been improved by some sort of interaction of this antigen with components in the Emunade dual adjuvant: mineral oil and Aluminium-hydroxide adjuvant, which interaction does not occur in an oily adjuvant without aluminium. This interaction may reduce (the effect of) substances in the PCV2 antigen that would otherwise cause injection-site reactions.

Therefore in a first aspect the invention relates to a process for preparing an antigen composition for a ready-to-use combination vaccine for swine, the composition comprising antigens of Mycoplasma hyopneumoniae (M. hyo) and of porcine circovirus type 2 (PCV2), characterised in that the process comprises a step of admixing a PCV2 antigen to a pre-formed antigen/adjuvant complex of an M. hyo antigen adsorbed to an Aluminium-hydroxide adjuvant.

For the invention "ready-to-use" means: not requiring the combining of (part of) the content of 2 or more containers in order to be ready for administration to a target animal. For example: not requiring a dissolution or an admixing step, and being available to the end-user as an emulsion in a single bottle.

For a ready-to-use vaccine, the necessary combining of compounds has been performed by the manufacturer of the vaccine, in a controlled environment. This has distinct advantages over field-side mixing, mainly in the ease of use for the end-user, especially when vaccinating large numbers of animals. Other advantages are that the manufacturer can perform the combining under aseptical conditions, and can apply various quality assurance tests on the final mixture, to guarantee its correct composition and its quality.

However this does not exclude that a ready-to-use vaccine may require some sort of simple pre-treatment, such as brief shaking by hand so as to remove sedimentation or creaming of an emulsion, or such as warming before administration when the vaccine had been stored refrigerated.

The term "swine" refers to animals of the family of Suidae, and preferably to animals of the genus Sus, which are also referred to as porcines. Examples are: a wild or a domestic pig, hog, wild boar, babirusa, or warthog. This also includes swine indicated by an arbitrary name, for example referring to their sex or age such as: sow, queen, boar, barrow, hog, gilt, weaner, or piglet.

The terms "Mycoplasma hyopneumoniae" (M. hyo) and "porcine circovirus type 2" (PCV2) refer to a bacterial respectively a viral micro-organism that displays the characterising features of its taxonomic group-members such as the morphologic, genomic, and biochemical characteristics, as well as the biological characteristics of that group, such as in their physiologic, immunologic, or pathologic behaviour. This also includes M. hyo bacteria, respectively PCV2 viruses that are sub-classified in any way, for instance as a subspecies, strain, isolate, genotype, variant, subtype or subgroup and the like.

Both micro-organisms are well known in the art, and are e.g. described in handbooks, like: "The Merck veterinary manual" (10th ed., 2010, C. M. Kahn edt., ISBN: 091191093X), and: "Diseases of Swine" (10th ed., 2012, J. Zimmerman et al., edt., ISBN-10: 081382267X).

It will be apparent to a skilled person that while an M. hyo bacterium, or a PCV2 virus for the present invention is currently classified in a particular species and genus, this is a taxonomic classification that could change in time as new insights lead to reclassification into a new or different taxonomic group. However, as this does not change the micro-organism itself, or its antigen repertoire, but only its scientific name or classification, such re-classified micro-organisms remain within the scope of the invention.

For the invention, "antigens of" a micro-organism can in principle be any type of antigenic material derived from an M. hyo bacterium or from a PCV2 virus, provided it can induce an immune response (either by itself or with an adjuvant). Preferably, the respective antigenic material is of a size, structure, form, or quality such that the immune response it induces in the vaccinated target swine is protective, i.e. is of sufficient strength to be able to prevent or reduce infection by M. hyo or PCV2 and associated signs of disease.

The antigens for use in the present invention can be an inactivated micro-organism, or can be a part thereof such as a subunit, extract, fraction, homogenate or sonicate. The antigen can contain one or more types of molecules such as protein, lipoprotein, glycoprotein, and nucleic acid. The antigen may be of biologic or of (semi-)synthetic origin, and may be derived directly or indirectly from a micro-organism such as an M. hyo bacterium, or a PCV2 virus.

An example of an M. hyo antigen is a bacterin. This can be produced according to methods well-known in the art, by the inactivation of the whole or a part of a bacterial culture. Inactivation can be done by treatment with any suitable technique such as with heat, radiation, or with chemicals such as formalin, beta-propiolactone, binary ethyleneimine (BEI), or beta-ethanolamine. The resulting bacterin is then a complex mixture of killed bacterial cells both intact and damaged, cell-fragments, cellular content, and factors secreted from the cells during culture, as well as factors from the culture medium and its various components.

An example of a PCV2 antigen is a subunit vaccine, e.g. based on the viral capsid protein, as is commonly applied in the field. This can be produced by recombinant expression of the viral ORF2 genomic sequence, e.g. by the baculovirus/insect cell system. Self-assembled VLP's can then be isolated from the insect cell culture, e.g. using centrifugation.

The term "comprises" (as well as variations such as "comprise", "comprising", and "comprised") as used herein, refer(s) to all elements, and in any possible combination conceivable for the invention, that are covered by or included in the text section, paragraph, claim, etc., in which this term is used, even if such elements or combinations are not explicitly recited; and does not refer to the exclusion of any of such element(s) or combinations. Consequently, any such text section, paragraph, claim, etc., can also relate to one or more embodiment(s) wherein the term "comprises" (or its variations) is replaced by terms such as "consist of", "consisting of", or "consist essentially of".

The "antigen/adjuvant complex" refers to the macromolecular structure that is formed upon the adsorption of (components of) an M. hyo antigen to an Aluminium-hydroxide adjuvant, as defined herein. Because this adsorption occurs by a number of physical- and chemical interactions, therefore the complex cannot be exactly defined in chemical terms. The composition and structure of the complex are also dependent on the composition and the characteristics of the antigen and the adjuvant used, as well as from the conditions under which it was formed. This is well-known in the art, and accepted in the field. Required and preferred characteristics of the antigen and the adjuvant, and of the conditions for the forming of their complex, are described herein.

The term "pre-formed" indicates that the forming of the antigen/adjuvant complex which this term refers to, had occurred at an earlier point in time. For the invention this means that the complex between an M. hyo antigen and an Aluminium-hydroxide adjuvant had been formed before any PCV2 antigen is added to the composition, and thus the forming of the complex occurs in the absence of a PCV2 antigen.

The inventors speculate this allows a given M. hyo antigen to become adsorbed to the Aluminium-hydroxide adjuvant as completely as is possible under the circumstances, without interference from or co-capture of the PCV2 antigen. Result is that in a vaccine prepared from the antigen composition according to the invention, the immune-response against the M. hyo antigen is optimal.

General conditions for adsorbing an antigen to an Aluminium-hydroxide adjuvant are well-known in the art, for instance from pharmaceutical handbooks, from governmental directives on the production of (human) vaccines, and from the instructions of the adjuvants' manufacturers. However, Aluminium-hydroxide adjuvant and M. hyo bacterin antigen do not have a highly defined composition. This makes that it is hard to define very specifically the process conditions, and the end-levels to be obtained for the forming of the antigen/adjuvant complex for the invention. Nevertheless, a person skilled in the art of making pharmacological formulations, such as a biochemist or pharmacist, or a team with such skills, will readily be able to vary and optimise these conditions, to achieve the maximal adsorption possible for a given M. hyo antigen and Aluminium hydroxide adjuvant. The level of adsorption achieved can then be determined, so that the effect of different conditions and materials can be compared.

For example, whether any M. hyo antigen has in fact adsorbed to Aluminium-hydroxide adjuvant, and if so how much, can conveniently be determined by biochemical methods, because Aluminium-hydroxide crystals can easily be pelleted by centrifugation. This allows the determination of the amount of M. hyo antigen in that pellet, indicating the extent of the formation of the antigen/adjuvant complex; alternatively this allows the determination of the amount of M. hyo antigen remaining in the supernatant, when complex-formation had not occurred, or was not complete.

Detection of M. hyo antigens in pellet or supernatant can be done using antibody-based methods, for example using Elisa, as outlined in the Examples. An alternative is to dissociate any bound M. hyo antigen from the Aluminium-hydroxide adjuvant in the pellet, and analyse the released antigen, e.g. using electrophoresis. Such dissociation is possible in different ways, e.g. by adapting pH, using phosphate ions, or by sonication of the pellet. All as described in the art.

Further optimisation is possible by testing how much of the adsorptive capacity of the Aluminium-hydroxide adjuvant has in fact been used under certain conditions of complex forming with an M. hyo antigen. This can be done by a subsequent complex formation using a defined amount of a known protein, and determining how much of that test protein can additionally be bound; for example using the binding assay as described in Ph. Eur. monograph 1664. This will indicate if, and how much, adsorption capacity has not been used.

For a given M. hyo antigen or a given Aluminium-hydroxide adjuvant, complex forming is as complete as possible when the amount of M. hyo antigen in the antigen/adjuvant complex cannot substantially be further increased, e.g. by adapting parameters of the adsorption, such as temperature, pH, duration or the relative amounts of the components. In addition, complex forming is as complete as possible when the binding capacity of the Aluminium-hydroxide adjuvant is used for as much as possible by M. hyo antigen, and cannot substantially be further decreased.

For example, an antigen composition can be produced according to a process of the invention. This can be centrifuged, after which pellet and supernatant can be tested separately. By using a polyclonal rabbit anti M. hyo antiserum, dilution ranges of supernatant, or resuspended pellet can be tested, for example in an Elisa set-up, for the relative amount of M. hyo antigen detectable.

Certain conditions were found to be helpful in optimising the forming of the antigen/adjuvant complex of M. hyo antigen and Aluminium-hydroxide adjuvant.

Therefore, in an embodiment of the process according to the invention, the antigen/adjuvant complex is pre-formed by the steps of:
a. admixing the Aluminium-hydroxide adjuvant and the *M. hyo* antigen, in a watery carrier at a pH at which the Aluminium-hydroxide adjuvant is positively charged, and
b. incubating the mixture of step a. to allow the adsorption of the *M. hyo* antigen to the Aluminium-hydroxide adjuvant and form an antigen/adjuvant complex.

The "watery carrier" can in principle be any watery liquid, provided it allows an effective and complete forming of the antigen/adjuvant complex. In a preferred embodiment, the watery carrier is relatively simple, containing only buffers or salts in purified water, e.g. the watery carrier is a physiological buffer, such as a balanced salt solution, or is a physiological salt solution, a.k.a. 'normal saline'; this is well-known and has 0.85% w/v sodium chloride in purified water. For the invention, a liquid is 'watery' if it consists for more than 50% of its volume or weight of water.

'Purified water' is preferably 'water for injection'; typically this is prepared from distilled water, double distilled water, micro-filtration water, or osmosis-purified water, that is sterile and essentially free from pyrogens.

As is known in the art: "positively charged" relates to a compound having a net positive charge in aqueous solution, under defined conditions.

The pH range in which Aluminium-hydroxide adjuvant is positively charged is from 0 to about 11, where 11 is the point of zero charge. Consequently, in conditions up to a pH of about 11, *M. hyo* antigen can bind effectively to Aluminium-hydroxide adjuvant. However, as some denaturation of the *M. hyo* antigen may occur at high or low pH levels, a more physiological pH is preferred. Therefore the pH of the watery carrier is preferably between 5 and 10, more preferably between 5.5 and 9, between 6 and 8, or even between 6.2 and 7.8. Most preferred is a pH of the watery carrier between about 6.5 and about 7.5. At these values the *M. hyo* antigen is maintained in physiological conditions, while the Aluminium-hydroxide adjuvant is still positively charged so that the *M. hyo* antigen can adsorb effectively.

The conditions for "incubating the mixture of step a." are also not very critical, although an effective formation of the antigen/adjuvant complex is required.

The inventors have found that the adsorbing of an *M. hyo* antigen to an Aluminium-hydroxide adjuvant starts quickly after both components are mixed, but to achieve complete adsorption, adequate time is needed. Therefore, the preferred period for incubating a mixture as described in step a., is for at least 15 minutes, more preferred: for at least 0.5, 1, 2, 4, 6, 8, 10, 12, 14, 16, 18, 20 or 24 hours, in this order of preference. Under practical circumstances, the incubation is preferably performed "overnight", which corresponds to a period of between about 12 and about 18 hours.

The inventors have also found that the adsorption of *M. hyo* antigen to an Aluminium-hydroxide adjuvant has a relatively wide tolerance for the incubation temperature; effective adsorption was observed both when refrigerated at 4° C. as well as at room temperature. However, as is well-known in the art Aluminium-hydroxide adjuvant should not be allowed to freeze, as that will damage the crystalline structure. Also, at temperatures far above normal mammalian body temperature, which for pigs is between 38 and 40° C., some denaturation of the *M. hyo* antigen could occur. Therefore the preferred temperature for incubating a mixture as described in step a., is between about 2 and about 45 degrees Celsius. More preferred is between 4 and 40° C., or even between 10 and 38° C. Most preferred is at 'room temperature', a.k.a. 'ambient temperature', which is between about 15 and about 30° C.

To accommodate for the viscous nature of the gel that is the Aluminium-hydroxide adjuvant, the incubation of the mixture of step a. in the process according to the invention, is preferably performed while the mixture is in motion. However, as is well-known in the art, violent mixing of Aluminium-hydroxide adjuvant may damage the crystalline structure. Therefore some sort of gentle agitation of the mixture is preferred. An example is stirring using a magnetic rod, or with various forms of shakers or tables that provide a gentle orbital, or rocking motion. All these are commonly available. For the invention, a gentle agitation is—for a stirring or spinning motion—250 rpm or less, preferably 150 rpm or less; one 'rotation' is a full circular motion, until returned in the starting position. For a rocking motion: 200 cycles/minute or less, preferably 100 cycles/minute or less. One 'cycle' is a full sequence of an up- and a down motion, until returned to the starting position.

With regard to the antigens used in the process according to the invention:

The *M. hyo* antigen is preferably a bacterin that was prepared from a whole culture; the bacterin is preferably inactivated with BEI; the bacterin is preferably concentrated to about 10-30 times using e.g. (ultra)filtration or dialysis. As discussed, the composition of a bacterin is not exactly known, but it can be characterised e.g. by indicating the number of *M. hyo* cells in the culture at the time of inactivation, and be corrected for the times of concentration. For the invention, the *M. hyo* antigen, when in the form of a bacterin, is derived from a culture of *M. hyo* containing between $10^1$ and $10^{10}$ *M. hyo* cells per ml in the total culture. Preferably between $10^4$ and $10^{10}$; $10^6$ and $10^{10}$; $10^7$ and $5 \times 10^9$; and between $5 \times 10^7$ and $5 \times 10^9$ *M. hyo* cells/ml in the total culture, in this order of preference. The *M. hyo* antigen used for the antigen composition according to the invention is taken from the inactivated suspension of such a culture. This may also be concentrated by filtration or centrifugation.

Preferably, the amount of *M. hyo* antigen to be added in step a. is calculated with consideration of the later incorporation of the antigen composition obtainable by the process into a vaccine. This means that when the final vaccine also contains a volume of an oily phase, the amount of *M. hyo* antigen in the antigen composition is compensated for that later dilution.

The volume of *M. hyo* bacterin from the inactivated and concentrated culture can be between 1 and 50% v/v, relative to the volume of a final vaccine composition. Preferably the amount is between 2 and 40%, between 3 and 30%, between 4 and 20%, or between about 5 and about 15% v/v relative to the volume of a final vaccine composition, in this order of preference.

The *M. hyo* antigen is preferably selected from the *M. hyo* J strain, strain 11, or strain 232. More preferably the *M. hyo* antigen is from J strain.

Therefore, in a preferred embodiment of the process according to the invention, the *M. hyo* antigen is a bacterin, is prepared by chemical inactivation of an *M. hyo* culture from the J strain, at a cell density of between about $10^7$ and about $10^9$ cells/ml, after which the inactivated culture is concentrated by filtration to between 10-20 times, and the inactivated, concentrated culture is used at between about 5 and about 10% v/v relative to the volume of a final vaccine composition comprising the *M. hyo* antigen.

The PCV2 antigen is preferably an ORF2 encoded subunit, and is preferably in the form of a VLP. The VLP antigen preferably is not highly purified. The amount of PCV2 antigen to be admixed in step b. of the process according to the invention is preferably between about 2 and about 200 µg/ml of PCV2 ORF2 VLP. More preferred is between 4 and 100 µg/ml of PCV2 ORF2 VLP.

As for the M. hyo antigen, the amount of PCV2 antigen to be added is preferably calculated with consideration of the later incorporation of the antigen composition obtainable by the process into a vaccine. This means that when the final vaccine also contains a volume of mineral oil, the amount of PCV2 antigen in the antigen composition is compensated for that later dilution. For the amount of PCV2 antigen to be added to step b., this is such that a final vaccine contains at least 20 µg ORF2 VLP/dose.

As the PCV2 antigen is only partially purified, therefore this could be a sample from an inactivated insect cell/baculovirus culture, after centrifugation, containing between 50 and 1000 pg/ml of total protein. Also, in practical terms this means a volume of PCV2 antigen that is between about 3 and about 30% v/v relative to the volume of a final vaccine composition. More preferably between 5 and 25, or even between about 10 and about 20% v/v relative to the volume of a final vaccine composition.

Therefore, in a preferred embodiment of the process according to the invention, the PCV2 antigen is an ORF2 encoded subunit antigen, in the form of a VLP, is harvested from an insect cell/baculovirus expression culture that was chemically inactivated and centrifuged, and has at least 20 µg ORF2 VLP per animal dose in a final vaccine composition comprising the PCV2 antigen.

There is no particular relationship between the M. hyo- and the PCV2 antigens, such as in their type or amount per dose. Consequently, their type and/or relative amounts in the antigen composition according to the invention can be varied independently, when appropriate; provided they allow the effective forming of the antigen/adjuvant complex, and provide an effective vaccination effect.

To determine the amount of antigen from a batch of M. hyo or PCV2 antigen that needs to be used for the preparation of the antigen composition and the vaccine according to the invention, typically an in vitro potency assay is used. This can also serve to ascertain that a new batch of M. hyo or PCV2 antigen has the required antigenic mass. Such an internal batch release test is usually an antigenic mass Elisa. This can for example be done using a polyclonal antiserum raised against M. hyo or PCV2, for example obtained by immunisation of rabbits, and using a reference standard of M. hyo or PCV2 antigen. The potency of the reference antigen had been determined in a series of vaccination-challenge experiments, so that a certain number of arbitrary units of antigen can be coupled to a desired vaccination efficacy. An example is the wording of the registration file: a vaccine according to the invention needs to contain at least 2.7 'relative potency units' of M. hyo bacterin antigen, and at least 2800 'antigenic units' of PCV2 antigen per vaccine dose of 2 ml. These amounts of antigen, comprised in a vaccine according to the invention, had been determined to assure effective protection against severe challenge infection with M. hyo and PCV2 as described herein.

To obtain the required potency per animal dose of the vaccine according to the invention, typically an M. hyo bacterin antigen is used at between 5 and 15%, and a PCV2 antigen at between 10 and 20% of the volume of a final vaccine composition comprising those antigens.

The development of such a batch release test, including the preparation of appropriate antisera and reference standards is well within the routine capabilities of the skilled person.

The amount of Aluminium-hydroxide adjuvant to be mixed with the M. hyo antigen needs to be sufficient to allow as complete as possible adsorption of the M. hyo antigen. On the other hand, the amount of Aluminium-hydroxide adjuvant used needs to be within acceptable limits of amount of aluminium per animal dose, and needs to be compatible with the formulation of a vaccine using the antigen composition obtainable by the process according to the invention. In a preferred embodiment, the mixture of step a. contains an amount of Aluminium-hydroxide adjuvant corresponding to an amount of aluminium between about 0.1 and 10 mg/ml; preferably an amount of aluminium between about 0.5 and 5 mg/ml. To achieve this, for example a commercial Aluminium-hydroxide adjuvant product can be used such as Alhydrogel™, which in one variant is available as a "2%" solution. This naming is slightly confusing, but is derived from the product containing about 2% w/w Aluminium oxide, which corresponds to about 3% w/w Aluminium hydroxide, and about 1% w/v Aluminium. Such a product can be used at a volume of between 3 and 30% v/v relative to the volume of a final vaccine composition. Preferably an Aluminium hydroxide adjuvant product is used at between 4 and 20% v/v, preferably at between about 5 and about 15% v/v relative to the volume of a final vaccine composition.

Therefore in a preferred embodiment of the process according to the invention, the antigen composition comprises amounts of M. hyo antigen between 5 and 15% v/v, of Aluminium hydroxide adjuvant product between 5 and 15% v/v, and of PCV2 antigen between 10 and 20% v/v, all relative to the volume of a final vaccine composition.

In an embodiment, the antigen composition according to the invention is used as the basis for a complete waterphase of a vaccine that is prepared from this antigen composition. Consequently, when the vaccine to be prepared is an emulsion comprising for example 10 or 20% of an oily phase, the waterphase forms 90 or 80% respectively of that final vaccine composition. Comprised in that waterphase is the antigen composition according to the invention, with the complex of M. hyo antigen and Aluminium hydroxide adjuvant, a watery carrier and PCV2 antigens. The exact volume amounts of the different compounds in the antigen composition according to the invention can vary, for example the relative volume of M. hyo or PCV2 antigen used may vary, dependent on the potency of a particular antigen batch being used, as described above. In addition the waterphase for the vaccine can also comprise other components such as fillers, stabilisers, preservatives, surfactants, additional antigen, and any other compound or solution needed in the preparation of a final vaccine prepared therefrom. For the invention, differences in volume of the components of the waterphase for a vaccine prepared therefrom, are compensated by adapting the volume of the watery carrier, to arrive at a desired total volume of the waterphase.

The inventors have found that it is favourable to perform the formation of the antigen/adjuvant complex for the invention in a relatively low volume; this allows optimal contact for the adsorption of the M. hyo antigen to the Aluminium hydroxide adjuvant. However, because of the gelatinous nature of Aluminium hydroxide adjuvant, the use of a mixture of only M. hyo antigen and a volume of commercial Aluminium hydroxide adjuvant product may not give the best results, and the adjuvant usually needs to be diluted somewhat. Therefore the formation of the antigen/adjuvant complex is performed in a mixture which also comprises a watery carrier.

As described, this watery carrier is also used to adjust the volume of the waterphase for the formation of a vaccine prepared therefrom.

In a preferred embodiment, the formation of the antigen/adjuvant complex for the invention is performed in a mixture with the watery carrier, but wherein the volume of watery carrier present during the formation of the complex is less than the total volume of watery carrier that will be used to form the complete waterphase for a later vaccine. This means that where the complete waterphase for a vaccine comprises a certain volume X of the watery carrier, then for the formation of the antigen/adjuvant complex, less than that volume X of the watery carrier is used; preferably 75% of volume X, more preferably 50, 40, 33, 30, 25, 20 or even 10% of volume X is used, in that order of preference. The remainder of the volume of watery carrier can then be added to the antigen composition after the formation of the antigen/antibody complex.

The inventors have also found that it is advantageous to the formation of the complex of M. hyo antigen and Aluminium hydroxide adjuvant, to keep the mixture of step a. as simple as possible, meaning: it is preferred to not yet include into the mixture any of the other components that would make up the complete waterphase, before the forming of the antigen/adjuvant complex. Such other components could be fillers, stabilisers, preservatives, surfactants, additional antigens, etc.

Consequently, in a preferred embodiment, the mixture of step a. of the process according to the invention, consists of an M. hyo antigen and an Aluminium-hydroxide adjuvant (both of which may already contain an amount of a watery carrier), and a watery carrier.

Examples of compounds which may need to be added to the waterphase, prior to emulsification into a final vaccine, but which are preferably added only after the formation of the M. hyo antigen/Aluminium hydroxide adjuvant complex, are: stabilisers such as ethanol or glycerol, additional antigens, or a surfactant such as Tween™.

Therefore, in a preferred embodiment of the process according to the invention, one or more, or all, of the following conditions apply:
  the M. hyo antigen is an M. hyo bacterin,
  the PCV2 antigen is encoded by PCV2 ORF2,
  the PCV2 ORF2 encoded antigen is a virus-like particle,
  the watery carrier of step a. is a balanced salt solution,
  the pH of the watery carrier of step a. is between 6 and 8,
  the volume of the watery carrier used in step a. is less than the total volume of watery carrier to be used for the formation of a waterphase for a final vaccine,
  the mixture of step a. is essentially free of other components,
  the incubation of step b. is for a period between 10 and 20 hours
  the incubation of step b. is at room temperature, and/or
  the incubation of step b. comprises a gentle agitation of the incubated mixture.

In a preferred embodiment of the process according to the invention, the antigen/adjuvant complex is pre-formed by the steps of:
  a. admixing an Aluminium-hydroxide adjuvant and an M. hyo bacterin, in physiological saline, at a pH between 6.5 and 7.5, and
  b. incubating the mixture of step a. to allow the adsorption of the M. hyo bacterin to the Aluminium-hydroxide adjuvant and form an antigen/adjuvant complex, whereby the temperature is between 15 and 30° C., and the incubation is during 12-18 hours, with gentle agitation of the mixture.

For the invention, being 'essentially free' of a compound means: not comprising any substantial amount of a compound, such as: less than 10% by weight or by volume of a compound, depending on whether the compound is a liquid or a solid. Preferably essentially free means comprising less than 8, 6, 5, 4, 3, 2, 1, 0.9, 0.8, 0.7, 0.6, 0.5, 0.4, 0.3, 0.2, 0.1, 0.09, 0.05, 0.01, or even less than 0.001% by weight or by volume of a compound, in this order of preference.

As the skilled person will appreciate, the process according to the invention can be performed by applying the steps as specified herein; in chronological order that is: mixing M. hyo antigen and Aluminium-hydroxide adjuvant in a watery carrier, incubating them to form an antigen/adjuvant complex, and adding PCV2 antigen to the pre-formed complex; all these as defined herein.

However one or more steps can also be added or inserted, to the beginning, middle or end of the process, e.g. to expand or optimise this process. For example: after step b. the pre-formed antigen/adjuvant complex can be stored, or can be purified, when needed, for example by centrifugation and resuspension. All this remains within the scope of the invention.

By the process according to the invention, an antigen composition can be produced, that can be the basis of a waterphase that can be used for the preparation of a ready-to-use combination vaccine for swine, which vaccine can prevent or reduce infection by M. hyo or PCV2 and associated signs of disease, already after a single dose.

Therefore in a further aspect the invention relates to an antigen composition obtainable by a process according to the invention. The antigen composition comprises a PCV2 antigen and an antigen/adjuvant complex of M. hyo antigen adsorbed to Aluminium-hydroxide adjuvant, all as defined herein.

The antigen composition according to the invention differs from prior art compositions in that it comprises an antigen/adjuvant complex of an M. hyo antigen and an Aluminium-hydroxide adjuvant, wherein the M. hyo antigen is adsorbed to the Aluminium-hydroxide adjuvant as completely as is possible for a given batch of M. hyo antigen and a given Aluminium hydroxide adjuvant.

Therefore in a preferred embodiment, the antigen composition according to the invention is characterised in that at least 50% of the M. hyo antigen present in the antigen composition is located in the antigen/adjuvant complex, adsorbed to Aluminium-hydroxide adjuvant.

This can be confirmed by testing: after centrifugation of the antigen composition according to the invention for 1-2 minutes at 1000-2000×g, and detection of M. hyo antigen by appropriate sero-diagnostic methods as described herein, at least 50% of the M. hyo antigen in the antigen composition is located in the pellet.

This is indicative of the relative amount of the M. hyo antigen that is located in the antigen/adjuvant complex, where it is adsorbed to Aluminium-hydroxide adjuvant.

Preferably the relative amount of M. hyo antigen of the antigen composition according to the invention that is present in the antigen/adjuvant complex, adsorbed to Aluminium-hydroxide adjuvant, is more than 60%; more preferably: is more than 70, 80, 85, 90, 95, 96, 97, 98, 99, or is 100%, in that order of preference.

Therefore in a preferred embodiment, the antigen composition according to the invention is characterised in that 100% of the *M. hyo* antigen in the composition, is located in the antigen/adjuvant complex, adsorbed to Aluminium-hydroxide adjuvant.

As the skilled person will understand, the complement of these percentages applies to the presence of *M. hyo* antigen remaining in the supernatant of the antigen composition according to the invention after centrifugation: when more than 50% of the *M. hyo* antigen present in the composition is located in the pellet, then logically less than 50% of the *M. hyo* antigen in the antigen composition is present in the supernatant.

Therefore in an embodiment, the antigen composition according to the invention is characterised in that less than 50% of the *M. hyo* antigen in the composition, is not located in the antigen/adjuvant complex, adsorbed to Aluminium-hydroxide adjuvant, respectively: is located in the supernatant after centrifugation.

Preferably the relative amount of *M. hyo* antigen of the antigen composition according to the invention that is not located in the antigen/adjuvant complex, adsorbed to Aluminium-hydroxide adjuvant, is less than 40%; more preferably: is less than 30, 20, 15, 10, 5, 4, 3, 2, 1, or is 0%, in that order of preference.

For the invention, the preferred way to characterise the antigen composition according to the invention is by determining the relative amount of *M. hyo* antigen that is adsorbed to Aluminium-hydroxide adjuvant.

However, in addition, the antigen composition according to the invention differs from prior art compositions in that it comprises an Aluminium-hydroxide adjuvant of which the binding capacity is used for as much as possible by *M. hyo* antigen.

Therefore, in an embodiment the antigen composition according to the invention comprises an Aluminium-hydroxide adjuvant of which the protein binding capacity is used for more than 50% by an *M. hyo* antigen.

This can be detected by testing (as described), by applying a further adsorption with a known amount of a known protein, and detecting by appropriate sero-diagnostic methods how much of the known protein can additionally be adsorbed to the Aluminium-hydroxide adjuvant in the antigen composition to be tested.

This is indicative for the unused protein binding capacity of the Aluminium-hydroxide adjuvant in the antigen composition according to the invention.

Preferably the protein binding capacity of the Aluminium-hydroxide adjuvant in the antigen composition according to the invention, is used for more than 60% by an *M. hyo* antigen; more preferably: for more than 70, 80, 85, 90, 95, 96, 97, 98, 99, or for 100% by an *M. hyo* antigen, in that order of preference.

In its most advantageous utility, the antigen composition according to the invention, or the antigen composition as obtainable by the process according to the invention, can be used to produce a vaccine for swine that is effective in preventing or reducing infection by *M. hyo* or PCV2 and in preventing or reducing associated signs of disease, is safe to use, is economically feasible, and is user-friendly in that it is ready-to-use.

Therefore in a further aspect the invention relates to a ready-to-use vaccine for swine, for preventing or reducing infection by *M. hyo* or PCV2 and associated signs of disease, the vaccine comprising the antigen composition obtainable by a process according to the invention, or the antigen composition according to the invention, and an additional adjuvant.

The "additional adjuvant" is additional in the sense that it is used in addition to the Aluminium-hydroxide adjuvant that is already in the antigen composition. This additional adjuvant ensures that the vaccine according to the invention is at least as efficacious as prior art single-antigen vaccines against PCV2 or *M. hyo*.

An "adjuvant" is a well-known vaccine ingredient that stimulates the immune response of a target in a non-specific manner. Many different adjuvants are known in the art. Examples of adjuvants are: Freund's Complete and -Incomplete adjuvant, vitamin E, non-ionic block polymers and polyamines such as dextran sulphate, Carbopol™, pyran, Saponin, such as: Quil A™, or Q-vac™. Saponin and vaccine components may be combined in an ISCOM™.

Furthermore, peptides such as muramyldipeptides, dimethylglycine, tuftsin, are often used as adjuvant, and mineral oil e.g. Bayol™, Drakeol™, Klearol™, or Marcol™, Montanide™ or light mineral (paraffin) oil; non-mineral oil such as squalene, squalane; vegetable oils or derivatives thereof, e.g. ethyl-oleate. Also combination products such as ISA™ from Seppic or DiluvacForte™ can advantageously be used.

A handbook on adjuvants and their uses and effects is: "Vaccine adjuvants" (Methods in molecular medicine, vol. 42, D. O'Hagan ed., 2000, Humana press, NJ, ISBN-10: 0896037355).

In an embodiment, a vaccine according to the invention is prepared as an emulsion of a watery- and an oily phase; preferably the emulsion is of the type: water-in-oil (w/o), oil-in-water (o/w), water-in-oil-in-water (w/o/w), or a double oil-emulsion (DOE). More preferred is a vaccine according to the invention that is an oil-in-water emulsion, whereby preferably the 'additional adjuvant' is the oily phase. Preferably the oil is a mineral oil.

The oily phase provides a depot effect in the vaccinated animal by slowly releasing the antigen, thereby providing a prolonged stimulation of the target's immune system. In this way, a vaccine that is an oil-in-water emulsion, advantageously displays properties of direct immune stimulation from the watery phase, and delayed immune stimulation from the oily phase.

Therefore, in an embodiment of a vaccine according to the invention, the vaccine is an oil-in-water emulsion.

In a further embodiment of a vaccine according to the invention, the additional adjuvant is a mineral oil.

Such adjuvants are known to have favourable effects on the immunogenicity of veterinary vaccines.

In an embodiment of a vaccine according to the invention, the vaccine is an oil-in-water emulsion and the additional adjuvant is a mineral oil.

In a preferred embodiment of a vaccine according to the invention, the mineral oil is a light- or white mineral oil or paraffin oil, commercially available under trade names such as: Marcol™ (ExxonMobil), Klearol™ (Sonneborn), or Drakeol™ (Penreco).

In an embodiment, the vaccine according to the invention comprises the antigen composition according to the invention at between 30 and 80% v/v relative to the volume of the final vaccine. Preferably between 40 and 75% v/v, between 45 and 70% v/v, between 50 and 65%, or even between 55 and 65% v/v, relative to the volume of the final vaccine, in this order of preference.

In an embodiment, the vaccine according to the invention comprises a mineral oil as additional adjuvant in an amount of between 3 and 50% v/v relative to the volume of the final vaccine. Preferably between 4 and 40% v/v, 5 and 30% v/v, 5 and 20% v/v, or even between 5 and 15% v/v, relative to the volume of the final vaccine, in this order of preference.

It goes without saying that other ways of adjuvanting, adding vehicle compounds or diluents, emulsifying or stabilizing a vaccine according to the invention are also within the scope of the invention.

The term "vaccine" implies the use of an immunologically effective amount of the antigens that it incorporates. What constitutes an 'immunologically effective amount' for the vaccine according to the invention depends on the desired effect and on the specific characteristics of the type of vaccine that is being used. Determination of the effective amount is well within the skills of the routine practitioner, for instance by monitoring the immunological response of the target following vaccination, or after a challenge infestation, e.g. by monitoring the targets' clinical signs and serological parameters, and comparing these to responses seen in unvaccinated challenged animals.

Whether a swine indeed suffers an infection with *M. hyo* and/or PCV2, and how severely, can be established by a qualified person, such as an experienced livestock breeder or a veterinarian, using the common knowledge on symptoms of disease, or using appropriate diagnostic tools.

Commonly vaccines also comprise a pharmaceutically acceptable carrier, which aids in the manufacture, application, or conservation of a vaccine, without causing (severe) adverse effects. Such a carrier can be the watery carrier as used in the process according to the invention. In a more complicated form, the carrier solution can e.g. be a buffer, which can comprise further additives, such as a stabiliser, preservative, or adjuvant. Details and examples are for instance described in well-known handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

An example of a ready-to-use PCV2/*M. hyo* combination vaccine according to the invention, is the Porcilis® PCV *M Hyo* (MSD AH) vaccine that will be marketed in 2015. This vaccine was found to display all the favourable characteristics of the invention, such as vaccine efficacy against *M. hyo* and PCV2 even after a single administration, with an excellent safety profile, it is ready-to-use, and is economically feasible. Details are described in the Examples, and in the CVMP assessment report for Porcilis PCV *M Hyo* (EMEA/V/C/003796/0000, 11 Sep. 2014). This report describes this novel vaccine to meet the criteria for vaccine efficacy against challenge infection with *M. hyo* and PCV2, even after 27 month of storage at 2-8° C. In a large number of laboratory- and field vaccination studies the vaccine was found to be safe upon intramuscular inoculation of a 2 ml dose, to piglets from about 3 weeks of age, in that no injection site-reactions were observed other than a swelling due to the inoculation volume, and no systemic reaction other than a transient and incidental increase of about 1° C. in rectal temperature. Also the vaccine was effective in that it was capable of reduction of vireamia, of virus load in lungs and lymphoid tissue, and of virus shedding caused by PCV2 infection, as well as reduction of severity of lung lesions caused by *M. hyo* infection. Further the vaccine reduced the loss of daily weight gain in the finishing period. The induced vaccine immunity was detectable for up to 22 weeks post inoculation, which covers the whole of the swine finishing period.

Therefore the veterinary medical effect of the vaccine according to the invention in swine is preventing or reducing infection by *M. hyo* or PCV2 and associated signs of either disease. This refers to the therapeutic and prophylactic effects that the vaccine according to the invention has: reducing the level of vireamia and infection, by reducing the replication and spread of *M. hyo* or PCV2; and reducing or even preventing clinical signs, such as lung lesions, pneumonia, reduction in ADWG and feed conversion, etc.

In a preferred embodiment, a vaccine according to the invention is for reducing lung-lesions caused by *M. hyo* infection and/or for reducing vireamia by PCV2 in swine.

A further advantageous effect of the vaccine according to the invention, is the prevention or reduction of the spread of *M. hyo* and/or PCV2 in a swine herd, both vertically to offspring, and horizontally within the herd or population, and within a geographical area. Consequently, the use of a vaccine according to the invention leads to a reduction of the prevalence of *M. hyo* and/or PCV2.

Therefore in a preferred embodiment, the vaccine according to the invention is capable of reducing the prevalence of *M. hyo* and/or PCV2 in a geographical area.

Also, further aspects of the invention are:

The use of a vaccine according to the invention for reducing the prevalence of *M. hyo* and/or PCV2 in a population or in a geographical area, and The vaccine according to the invention for reducing the prevalence of *M. hyo* and/or PCV2 in a population or in a geographical area.

In an embodiment a vaccine according to the invention may also comprise a stabiliser. This may serve to improve the characteristics of the vaccine emulsion, to protect degradation-prone components, and/or to enhance the shelf-life of the vaccine. Generally such stabilisers are large molecules of high molecular weight, such as lipids, carbohydrates, or proteins; for instance milk-powder, gelatine, serum albumin, sorbitol, sucrose, trehalose, spermidine, NZ amines, Dextrane or polyvinyl pyrrolidone, and buffers, such as alkali metal phosphates.

Preferably the stabiliser is free of compounds of animal origin, or even: is chemically defined, as disclosed in WO 2006/094.974.

A vaccine according to the invention may comprise a preservative, such as thimerosal, merthiolate, phenolic compounds, and/or gentamicin. Preferably no preservative is employed.

A vaccine according to the invention is preferably stable for at least 12 months, more preferably 18 months, or even 24 months. Being 'stable' refers to maintenance of chemical- and physical structure, and biological efficacy after prolonged storage under appropriate conditions; in particular: the maintenance of vaccine efficacy until the end of its recommended shelf-life.

It goes without saying that admixing other additives, that are required or beneficial to the pharmaceutical stability or effectiveness of the vaccine according to the invention, are also within the scope of the invention.

Target for the vaccine according to the invention are swine. The age, weight, sex, immunological status, and other parameters of the target to be vaccinated are not critical, although it is evidently favourable to vaccinate healthy, uninfected targets, and to vaccinate as early as possible to prevent any field infection with PCV2 or *M. hyo*. Because such an infection can be established already at young age, therefore the vaccine according to the invention is preferably applied from about 3 weeks old.

Advantageously, the efficacy of the vaccine according to the invention is not influenced by the level of maternally derived antibodies that the young swine may carry.

Therefore, a vaccine according to the invention can serve as an effective priming vaccination, which can later be followed and amplified by a booster vaccination. For example, the vaccine according to the invention can be administered at about 2-10 days of age, and again at about 3 weeks later, with each vaccination at a 1 ml volume. However, as the vaccine according to the invention is effective already after a single administration, a preferred embodiment is the administration of a single dose, e.g. of about 2 ml, from about 3 weeks of age. This vaccination protects pigs during the whole of the fattening period.

When the swine target of the vaccine according to the invention is intended to be kept for more than 6 months, such as sows for breeding, or boars for producing sperm, these can be administered a regular booster vaccination, 1, 2, or 3 times per year, e.g. for sows: one booster vaccination before each farrowing, which is on average about 2.2 times/year.

A vaccine according to the invention can thus be used either as a prophylactic- or as a therapeutic treatment, or both, as it interferes both with the establishment and with the progression of an infection by M. hyo, and/or by PCV2.

The regime for the administration of a vaccine according to the invention preferably is integrated into existing vaccination schedules of other vaccines that the target swine may require, in order to reduce stress to the animals and to reduce labour costs. These other vaccines can be administered in a simultaneous, concurrent or sequential fashion, in a manner compatible with their registered use.

A vaccine according to the invention, can be administered in a volume that is acceptable for the target animal, and can for instance be between about 0.1 and about 10 ml in volume. Preferably one dose is in a volume between about 0.1 and about 5 ml, more preferably one animal dose is between 0.2 and 3 ml. Preferably an intramuscular dose is between about 1 and about 3 ml, preferably about 2 ml; and an intradermal dose is between about 0.1 and about 0.5 ml, preferably about 0.2 ml.

The vaccine according to the invention can be administered to a target swine according to methods known in the art. Preferred application is by parenteral route, such as by injection into or through the skin, e.g.: intramuscular, intravenous, intraperitoneal, intradermal, submucosal, or subcutaneous. More preferred route of administration of the vaccine according to the invention is by intramuscular or by subcutaneous injection. Even more preferred is administration intramuscularly in the hind-leg, or in the neck.

It goes without saying that the optimal route of application will depend on the specifics of the vaccine that is used, and on the particular characteristics of the target.

In an embodiment, the vaccine according to the invention is administered intramuscularly to swine from about 3 weeks of age, as a single dose of about 2 ml.

Preferred site for intramuscular administration is the neck.

It is well within reach of the skilled person to further optimise a vaccine according to the invention. Generally this involves the fine-tuning of the efficacy of the vaccine, so that it provides sufficient immune-protection. This can be done by adapting the dose, volume, or antigen content of the vaccine; by using the vaccine in another form or formulation; by adapting the other constituents of the vaccine (e.g. the stabiliser or the additional adjuvant); or by application via a different route, method, or regime.

A vaccine according to the invention may additionally comprise other compounds, such as an additional antigen, a cytokine, or an immunostimulatory nucleic acid comprising an unmethylated CpG, etc. Alternatively, a vaccine according to the invention can advantageously be combined with a pharmaceutical component for example an antibiotic, a hormone, an anti-inflammatory- or an anti-parasitic drug. Or, the vaccine according to the invention, may itself be added to a vaccine.

The vaccine according to the invention can advantageously be combined with another antigen, e.g. derived from another pathogen. The advantage of such a combination vaccine is that it not only induces an immune response against M. hyo and PCV2, but also against other pathogens while only a single handling of the target animal for the vaccination is required, thereby reducing vaccination-stress to the target, as well as time- and labour costs.

Therefore, in a preferred embodiment, a vaccine according to the invention comprises additional antigenic material that is derived from a micro-organism pathogenic to swine.

The "additional antigenic material" may itself be in replicative or in inactivated form, or a subunit, and may be with or without an adjuvant. The additional antigenic material may be an antigen, and may consist of a biologic or synthetic molecule such as a protein, a carbohydrate, a lipopolysacharide, or a nucleic acid molecule. Alternatively it may be an expression product from a piece of nucleic acid from that other micro-organism, or a vector comprising such a piece of nucleic acid; the vector can be itself a micro-organism or a eukaryotic host cell.

The additional antigenic material can be "derived from" the other micro-organism pathogenic to swine in any way, e.g. as an extract, fraction, homogenate or sonicate.

A "micro-organism pathogenic to swine" for the invention, is well known in the art. The additional antigenic material may therefore be derived in principle from any virus, bacterium, parasite, fungus, rickettsia, protozoa and/or parasite that is pathogenic to swine.

Examples of such micro-organism pathogenic to swine are: porcine reproductive and respiratory syndrome virus, pseudorabies virus, porcine parvo virus, classical swine fever virus, swine influenza virus, foot-and-mouth disease virus, porcine epidemic diarrhoea virus, transmissible gastro enteritis virus, vesicular stomatitis virus, Lawsonia intracellularis, Actinobacillus pleuropneumoniae, Brachyspira, E. coli, Haemophilus, Streptococcus, Salmonella, Clostridia, Pasteurella, Erysipelothrix, Bordetella, Toxoplasma, Isospora, and Trichinella.

In a preferred embodiment the additional antigenic material is added to a vaccine according to the invention, as a non-live lyophilised antigen, which can be reconstituted by admixing the vaccine emulsion of the invention. This is described for example in WO 2010/106.095.

In a preferred embodiment of the vaccine according to the invention, the vaccine comprises antigens from M. hyo, PCV2, Lawsonia intracellularis, and PRRSV.

As these are important swine diseases, therefore their combination into a single shot ready-to-use vaccine is very favourable.

A vaccine according to the invention is prepared by means well-known to the skilled person.

Therefore, in a further aspect the invention relates to a process for preparing a vaccine according to the invention, comprising a step of admixing the antigen composition obtainable by a process according to the invention, or the antigen composition according to the invention, and an additional adjuvant.

In a further aspect the invention relates to a process for preparing a vaccine according to the invention, comprising a step of emulsifying the antigen composition obtainable by a process according to the invention, or the antigen composition according to the invention, and a mineral oil, into an oil-in-water emulsion.

Such processes result in the availability of a vaccine according to the invention, the vaccine having the favourable effect of preventing or reducing infection by *M. hyo* and/or PCV2 and associated signs of disease, in a swine, as described above.

Details and examples of "a process for preparing a vaccine" are described herein, which are readily applicable by a person skilled in the art. For example, the antigen composition according to the invention can be produced industrially in smaller or larger volumes, is then combined with pharmaceutically acceptable excipients, is formulated into a vaccine, and filled-out into appropriately sized containers. The various stages of the manufacturing process will be monitored by adequate tests, for instance by immunological tests for the quality and quantity of the antigens; by microbiological tests for inactivation, sterility, and absence of extraneous agents; and ultimately by studies in animals for confirming vaccine efficacy and safety. After completion of the testing for quality, quantity and sterility the vaccine product can be released for sale.

All these are well known to a skilled person, and general techniques and considerations that apply to the preparation of vaccines are described for instance in governmental directives and regulations (Pharmacopoeia) and in the well-known handbooks.

A vaccine according to the invention can be prepared into a form that is suitable for administration to a swine target, and that matches with the desired route of application, and with the desired effect.

Preferably a vaccine according to the invention is formulated into a form that is suitable for parenteral injection, i.e. an injectable liquid such as: a suspension, solution, dispersion, or emulsion. Commonly such vaccines are prepared sterile, and at physiological pH.

Therefore in further aspects the invention relates to:
The antigen composition obtainable by a process according to the invention, or the antigen composition according to the invention, for use in a vaccine for swine for preventing or reducing infection by *M. hyo* or PCV2 and associated signs of disease.
Use of the antigen composition obtainable by a process according to the invention, or the antigen composition according to the invention, for the manufacture of a vaccine for preventing or reducing infection by *M. hyo* or PCV2 and associated signs of disease.
Use of a vaccine according to the invention, or of a vaccine as obtainable by a process according to the invention, for preventing or reducing infection by *M. hyo* or PCV2 and associated signs of disease.
A method for preventing or reducing infection by *M. hyo* or PCV2 in swine and associated signs of disease, the method comprising the administration of a vaccine according to the invention, or of a vaccine as obtainable by a process according to the invention, to swine.

The invention will now be further described by the following, non-limiting, examples.

EXAMPLES

1. Preparation of *M. hyo* Antigen

*M. hyo* bacterin antigen was prepared in a way similar to that for the commercial M+Pac vaccine; this is essentially as described (WO 1993/016.726). In short: *M. hyo* strain J was cultured in suspension in a rich medium, based on the medium originally described by Friis (1975, supra). This is a complex medium that contains yeast extract, serum and various extracts of porcine and bovine origin. After several pre-cultures, the main culture was done in a large fermenter at 37° C. with agitation and pH control, and commonly took between 20 and 60 hours to reach the stationary phase. To inactivate the culture BEI was added to the fermenter, this was stirred for 1 hour, after which the complete content was transferred to a second vessel, and incubated up to 24 hours while stirred, at 37° C. Next excess BEI was neutralised using sodium-thiosulphate, by stirring up to 24 hours at 37° C. The inactivated and neutralised culture was then concentrated up to 15 times by ultrafiltration. The *M. hyo* bacterin antigen bulk was stored at 4° C. until use. The antigenic mass and relative potency was determined with an in-house Elisa, using an *M. hyo*-specific polyclonal rabbit antiserum, and by comparison to a reference standard *M. hyo* bacterin preparation of known potency.

2. Preparation of PCV2 Antigen

PCV2 antigen, in the form of a subunit that is ORF2 encoded VLP's, was produced in a way similar to that for Porcilis PCV; this is essentially as previously described (e.g. WO 2007/028.823). In short: a suspension culture of Sf21 insect cells was infected with a recombinant baculovirus comprising the PCV2 ORF2 gene inserted under the control of the baculoviral p10 gene promoter; cell density at the time of infection was about $1.4 \times 10^6$ cells/ml, the multiplicity of infection (MOI) was 0.01. After 4-8 days of culturing at about 27° C., the whole culture was sonified by passing it through an industrial scale sonifier. Next the recombinant baculovirus was inactivated with BEI at 37° C. for 72 hours, with stirring and pH control. After inactivation, the BEI was neutralised with sodium thiosulphate. After neutralization, cell debris was removed by centrifugation. Next the supernatant was used to determine the antigenic mass of the PCV2 capsid VLP's, using SDS gel-electrophoresis by comparison to a dilution range of a known amount of a marker protein, or an in-house Elisa.

3. Preparation of Antigen Composition of *M. hyo* and PCV2 Antigens, and Formulation of Ready-to-Use Vaccine An exemplary protocol to prepare an antigen composition according to the invention, and subsequently a vaccine according to the invention, is the preparation of a 100 ml batch of vaccine according to the invention, with 18% of oil phase, as follows: in a beaker glass were combined aseptically: 5 ml from a batch of *M. hyo* bacterin antigen at about 60 RPU/ml, 10 ml of Alhydrogel 2%, and 12 ml of normal saline. These amounts represent 3 RPU *M. hyo* antigen/ml and about 1 mg/ml of Aluminium in the final vaccine. These were combined with watery carrier, here: saline. As for this vaccine 37 ml saline would be added to complete the waterphase, here 33% of that volume, 12 ml was used for the formation of the antigen/adjuvant complex.

The mixture was adjusted to a pH of 6.5 using 4 N hydrochloric acid, and the mixture was incubated at room temperature (about 20° C.), overnight (16 hours), under gentle stirring using a magnetic mixing plate and a sterilised magnetic mixing bar. Next morning the mixture was combined with the remaining volume of saline, with 17 ml of a PCV2 antigen batch at about 14000 AU/ml (providing about 2300 AU/ml in the final vaccine), and with ethanol 96% and glycerol (sterilised). Mixing was continued for 10 minutes, after which the waterphase for the vaccine was ready. Next 18 ml of an oil phase was added, consisting of a mixture of Tween, Span, and Drakeol. Next the two phases were homogenized using an ultra-turrax mixer, for 2 minutes at 10.000 rpm.

Vaccine batches of larger volumes, up to 100 litres have been prepared in essentially the same way, and these were used in the various laboratory- and field-vaccination experiments as described herein. At this scale large sized mixing vessels were used to accommodate the larger volumes, and an adaptation was made to the time of the mixing of the pre-formed antigen/adjuvant complex with the PCV2 antigen and the other components of the waterphase: this was increased to 60 minutes; pH was maintained at between 6.2 and 7.5, and incubation was at room temperature. Also the volumes of the watery phase and of the antigen batches differed, to match the potency of the antigen batches used. Evidently also the emulsification of these volumes was performed using a large scale homogeniser (Dispax reactor, IKA).

Experiments continue to optimise the conditions of the process according to the invention, for the pre-forming of the antigen/adjuvant complex. For example by varying the temperature and the duration of the incubation, the pH of the mixture, and the ratio of Aluminium hydroxide adjuvant to M. hyo antigen.

Samples for testing if and how much M. hyo antigen has adsorbed to the Aluminium hydroxide adjuvant are then taken from the waterphase before emulsification, and are centrifuged and supernatant and pellet are tested. When the vaccine was prepared as an oil-in-water emulsion, this can also be done using samples of the final vaccine.

4. Effect of Different Conditions for Forming the Antigen/Adjuvant Complex

M. hyo/PCV2 combination vaccines were prepared as described above, using antigen compositions prepared using different processes: having the PCV2 antigen present or not during formation of the complex between M. hyo antigen and Aluminium hydroxide adjuvant. By testing these vaccines in experimental animals, this allowed a comparison of the effect by the different processes on the efficacy of the M. hyo antigen.

4.1. Materials and Methods

An antigen composition was prepared using 5% (of final vaccine volume) of a 10× concentrated batch of M. hyo bacterin, and a standard amount of PCV2 antigen, comparable to that in commercial PCV2 vaccines. Vaccines were prepared according to the following schedule:

| Vaccine | M.hyo antigen input (v/v) | PCV2 antigen amount (AU)/dose | Aluminium hydroxide complex forming: |
|---|---|---|---|
| A | 5% | — | M.hyo |
| B | 5% | >2800 | M.hyo + PCV2 |
| C | 5% | >2800 | M.hyo |

After the adsorption step, the remaining components of the waterphase were added, followed by addition of the oil phase and emulsification, to obtain the final vaccine product. The vaccines were stored at 2-8° C. until use.

Next, four groups of 8 piglets were used for the vaccination-challenge experiment: three groups each received one of the specific vaccines, one group served as unvaccinated control group. The three vaccines were administered intramuscularly as a 2 ml dose at three weeks of age.

Four weeks later, at 7 weeks of age, all pigs were challenged by intratracheal instillation of 5 ml of a culture of a virulent M. hyo isolate in Friis medium, on two consecutive days. Again three weeks later (at 10 weeks of age), the pigs were necropsied and consolidated M. hyo lung lesions were scored according to the Goodwin scale.

During the experiment, blood samples for serology were taken at the time of vaccination, at challenge, and at necropsy. Anti-PCV2 antibody levels were determined in arbitrary units using an Elisa.

4.2. Results

TABLE 1

Results of M.hyo lung lesions scores and PCV2 serology results

| Group | Mean M.hyo lung lesions score | % reduction comp. to Control | Anti-PCV2 titre (log2) at age: 3 wk | 7 wk | 10 wk |
|---|---|---|---|---|---|
| Vaccine A | 3.3 ± 4.6* | 66 | 6.7 ± 1.5 | 5.1 ± 1.1 | 2.9 ± 0.3 |
| Vaccine B | 6.8 ± 6.7 | 30 | 6.8 ± 1.6 | 8.1 ± 1.2 | 8.2 ± 1.1 |
| Vaccine C | 4.1 ± 3.5* | 58 | 6.9 ± 1.6 | 8.4 ± 1.0 | 8.6 ± 1.3 |
| Unvacc. Control | 9.7 ± 7.2 | 0 | 6.8 ± 1.6 | 5.3 ± 0.8 | 3.5 ± 1.0 |

*lesion score significantly different from control ($p < 0.05$, Mann-Whitney U test)

As is represented in Table 1, vaccination with the M. hyo single-antigen vaccine A resulted in a significant reduction of the severity of M. hyo-induced lung lesions of 66%, as compared to the severity of the lesions in the unvaccinated control pigs. This vaccine is comparable to the M+Pac commercial product. However for Vaccine B, prepared from an antigen composition where M. hyo antigen and PCV2 antigen were both present during the complex formation this was essentially different: this vaccine induced only 30% reduction of lung lesions. The M. hyo vaccine efficacy was restored to 58% lung lesion reduction, which is essentially the level of the single-antigen vaccine, for vaccine C; this vaccine was prepared from an antigen composition that had been prepared according to the process according to the invention.

With respect to the PCV2 antibody levels: the pigs in all groups had maternally derived antibodies against the PCV2 antigen at the time of vaccination. These maternal antibodies declined in the group receiving vaccine A and in the control group. The groups receiving vaccines B or C, containing PCV2 antigen, showed a seroresponse to a protective level. Among them there was no significant difference, indicating that PCV2 vaccine efficacy is not linked to the way antigens are adsorbed to the Aluminium hydroxide adjuvant.

4.3. Conclusions

There is a clear and significant difference in the vaccine efficacy against M. hyo infection, depending on the way the antigen composition is prepared: when PCV2 antigen was present during the adsorption of M. hyo antigen to Aluminium hydroxide, the resulting vaccine was only half as effective, as compared to when PCV2 antigen was added afterwards to pre-formed M. hyo antigen/Aluminium hydroxide adjuvant complex.

5. Extended Testing of the Safety and the Efficacy of a Ready-to-Use PCV2/M. hyo Vaccine The objective of the studies described below was to evaluate the efficacy and the safety of the new Porcilis PCV M Hyo vaccine, under laboratory and under field conditions.

5.1. Materials and Methods 5.1.1. Vaccine

The vaccine tested contained M. hyo bacterin antigen, baculovirus-expressed PCV2 ORF2 VLP antigen, and Emunade adjuvant, as described. The vaccine was administered intramuscularly in the neck, as a single 2 ml dose, to 3 week old piglets.

5.1.2. GLP Safety Trial

Two groups of 12 healthy SPF pigs were either vaccinated with Porcilis PCV M Hyo at 19-21 days of age (vaccinated group) or injected with phosphate buffered saline (control group). Until 14 days after vaccination, the piglets were observed daily for abnormal systemic or local reactions. Rectal temperature was recorded one day before vaccination, just before vaccination, 4 hours after vaccination and daily for four days. At 14 days post vaccination, all animals were sacrificed for examination of the injection site.

5.1.3. Immunization and Challenge Experiments

The onset of immunity (OOI) and duration of immunity (DOI) for each of the two vaccine antigens were determined in experimental challenge studies. In each experiment, 3 week old pigs from herds free of $M. hyo$ and seropositive for PCV2 were randomly divided in two groups (vaccine and control) at the time of vaccination (PCV2 OOI/DOI: 15 pigs per group, $M. hyo$ OOI: 19 animals per group, DOI: 40 pigs per group). Blood samples were taken just before vaccination, at the time of challenge and 2 (PCV challenge studies only) and 3 weeks after challenge. For the determination of the DOI blood samples were also taken at regular intervals between vaccination and challenge.

PCV2 challenge was done by intranasal instillation (3 ml per nostril, with about $10^6$ TCID50) of a recent Dutch PCV2 field isolate, at 5 or 25 weeks of age. Three weeks after PCV2 challenge, all pigs were necropsied and the mesenteric and inguinal lymph nodes, tonsil and lung were collected for quantification of the PCV2 viral load.

$M. hyo$ challenge was performed intratracheally on two consecutive days with 10 ml of a culture of a Danish field isolate (provided by Dr N. Friis, National Veterinary Laboratory, Copenhagen) containing about $10^7$ colour change units/ml (CCU/ml) at 7 or 24 weeks of age. Three weeks after challenge, the pigs were necropsied to evaluate lung lesions which were scored as described by Goodwin et al. (supra).

During all studies, the pigs were observed daily for clinical abnormalities.

5.1.4. Field Trials

A field safety trial was done in young piglets according to a randomized and blinded design in two pig farms in The Netherlands and one in Germany. In each farm, at least 56 healthy three-week-old suckling piglets aged 17-24 days were allocated randomly to one of two groups. The piglets in one group (vaccine) were vaccinated with Porcilis® PCV M Hyo and the piglets in the other group (control) were injected with sterile buffered saline. The general health of the piglets was checked at admission (one day before vaccination), immediately before vaccination, 1 and 4 hours after vaccination, and daily for 14 days. One day before vaccination, immediately before vaccination, 4 hours after vaccination, and daily for 4 days after vaccination, the rectal temperature of all piglets was measured. The injection site was examined for local reactions by palpation at 1 and 4 hours after vaccination, and then daily for 14 days. All study piglets were weighed individually at admission (day −1), and at the end of the study (21 days post vaccination).

Also a combined field safety and -efficacy study was performed according to a controlled, randomized and blinded design, in a French pig herd suffering from $M. hyo$ and PCV2 field infection. Healthy three week old suckling piglets were allocated randomly, within litters, to one of two groups of approximately 300 piglets each. The pigs in one group (vaccine) were vaccinated with Porcilis® PCV M Hyo and the pigs in the other group (control) were injected with sterile buffered saline. The primary efficacy parameters were lung lesions at slaughter, PCV2 vireamia and the average daily weight gain (ADWG) during fattening, (i.e. between 7 and 19 weeks post vaccination (wpv)). Secondary parameters were overall ADWG (i.e. between vaccination and 19 wpv), mortality, morbidity, pleurisy lesions and PCV2 shedding. Also the serological response to vaccination or field infection was determined. The pigs were weighed individually at vaccination, at transfer to the finishing unit, and before slaughter. Medication was recorded and pigs that died during the study were examined post mortem to establish the cause of death. The lungs were examined individually at slaughter to score the severity of typical $M. hyo$ lesions and pleurisy. Twenty five piglets per treatment group were bled for serum samples and rectal and nasal swabs were taken approximately every 4 weeks. Although safety was not the primary objective of this study, the investigator routinely observed the animals at vaccination and, as a group, at 4 hours after and 1, 4, 7 and 14 days after vaccination.

5.1.5. Serology

For $M. hyo$ serology, a commercial Elisa ($M. hyo$ Ab test, IDEXX) was used according to the manufacturer's instructions. Results are expressed as negative, positive or inconclusive.

For PCV2 serology, an in-house ELISA was performed as previously described (Haake et al., supra).

5.1.6. Quantification of PCV2 DNA

Quantification of the PCV2 viral load in serum, lymphoid organs, lungs and excretions were performed by qPCR as previously described (Haake et al., supra).

5.1.7. Statistical Analyses

The area under the curve (AUC) of the qPCR data for the serum samples collected after PCV2 challenge were calculated by the linear trapezoidal rule and analysed by the Wilcoxon Rank Sum test. Lung lesion scores in challenge experiments and the qPCR data of inguinal and mesenteric lymph nodes, lung and tonsil were also analysed by the Wilcoxon Rank Sum test.

In the field study, the AUC data were ranked before analysis using ANOVA with vaccination group, production batch and their interaction as fixed effects. Lung lesion scores in the field study were compared between the groups using mixed model ANOVA. Vaccination group, production batch and their interaction were included as fixed effects and the sow as random effect. The proportions of pigs with pleurisy (absent or present), the mortality and the morbidity were compared between the vaccination groups by Cochran Mantel Haenszel method with production batch as classification variable. The average daily weight gain was compared between the groups using a mixed model ANOVA. Vaccination group, production batch and gender with appropriate interactions were included as fixed effects, and sow as a random effect. The body weight at admission was included in the model as a covariate. The numbers of pigs with local or systemic reactions were compared with the Fischer's exact test.

5.2. Results 5.2.1. Safety Trials

The combined results of all safety studies are summarized in Table 1.

In the GLP safety study, none of the animals developed local or systemic reactions and no macroscopic abnormalities were observed at the injection site at necropsy. At 4 hours after vaccination, the rectal temperature of vaccinated animals was on average 1.1° C. higher than in the control animals (p<0.001) but returned to normal on the day after vaccination.

In the field safety study, treatment resulted in a local injection-site reaction with a maximum diameter of 1 cm in 13% of the vaccinates and 0.3 cm in 4% of the controls. These local reactions were observed at 4 hours post vaccination only and disappeared by the next day. The numbers of piglets with a deviation from the normal general health after treatment were similar in both groups (6% and 5% for vaccinates and controls, respectively). A 1.1° C. higher mean rectal temperature (p<0.0001) at 4 hours post vaccination was measured in the vaccinates (40.6° C. vs. 39.5° C.), which returned to normal on the day after vaccination. Weight gain was not different between groups during the three week observation period after treatment.

In the field safety and efficacy study, local reactions were observed in approximately 1% of the pigs in both groups. The maximum size of the local reactions in the vaccinates was 2 cm and the maximum duration was one day. A deviation from the normal general health was observed in 3% of the vaccinates and 1% of the controls. Some animals showed minor signs of discomfort 4 hours after vaccination.

5.2.2. Challenge Experiments

No clinical abnormalities that could be related to treatment were present in the periods between vaccination and challenge. However, some vaccinated and control pigs had lameness during the studies, most likely due to a Streptococcus suis infection. The PCV2 challenge infection did not result in any clinical signs, but the qPCR data clearly showed infection of the various lymphoid tissues and lung (FIG. 1). Mean viral loads were in general in the order of 2 to 3 log 10 lower in the vaccinated pigs, and the differences between the groups were statistically significant (p<0.05).

For Porcilis® PCV M hyo a PCV2, a specific antibody titre of about 3 Log 2 and higher correlates with significant reduction of viral load. In these experiments vaccination also resulted in a clear antibody response against PCV2 after vaccination, whereas the control group remained serologically negative after the decline of maternal antibody titres until the time of challenge. Following challenge, vaccinates developed an anamnestic response and the animals in the control group started to seroconvert.

Figure 2:
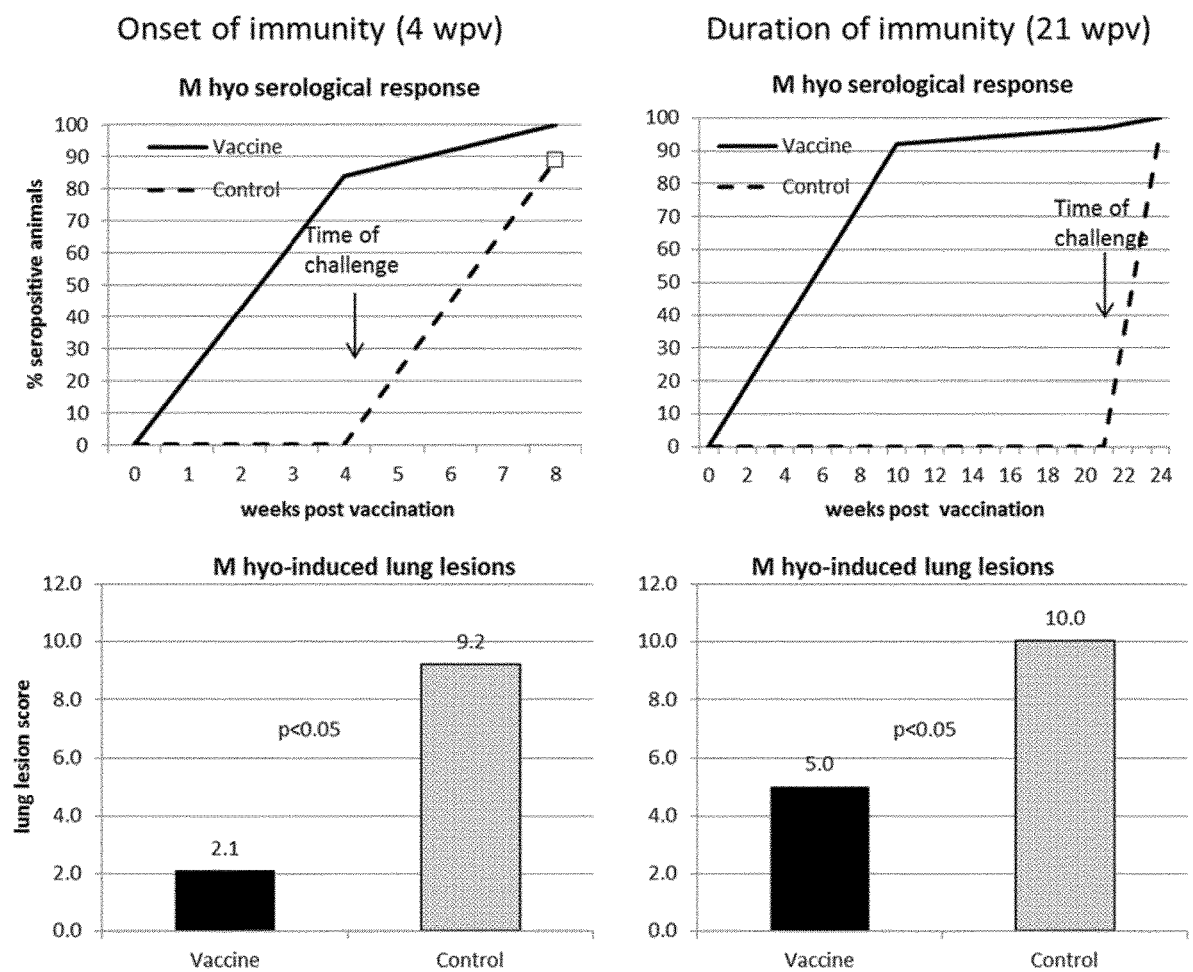

A seroresponse after vaccination was also seen in the M. hyo challenge experiment with 84% of animals seropositive at 4 wpv and 97% of animals seropositive at 21 wpv (FIG. 2). Almost all the control animals responded serologically to the challenge infection. At necropsy three weeks post challenge, the median M. hyo-induced lung lesions were 77% (001 study) and 50% (DOI study) lower than in the vaccinated groups (p<0.05).

5.2.3. Field Efficacy Study

The PCV2 serological profile of the pigs in the field study (FIG. 3) is indicative for a PCV2 field-infection between 8 and 12 wpv. Indeed, at 8 weeks post vaccination the presence of PCV2 could be detected at low amounts in control animals reaching a peak in nasal and faecal excretions at 12 wpv and in serum at 16 wpv. However, compared to the control animals the viral load of the vaccinated animals (calculated as AUC) was significantly reduced by 79% (p<0.0001), 70% (p<0.0001) and 55% (p=0.0159) in serum, nasal and faecal excretions, respectively.

Figure 4:
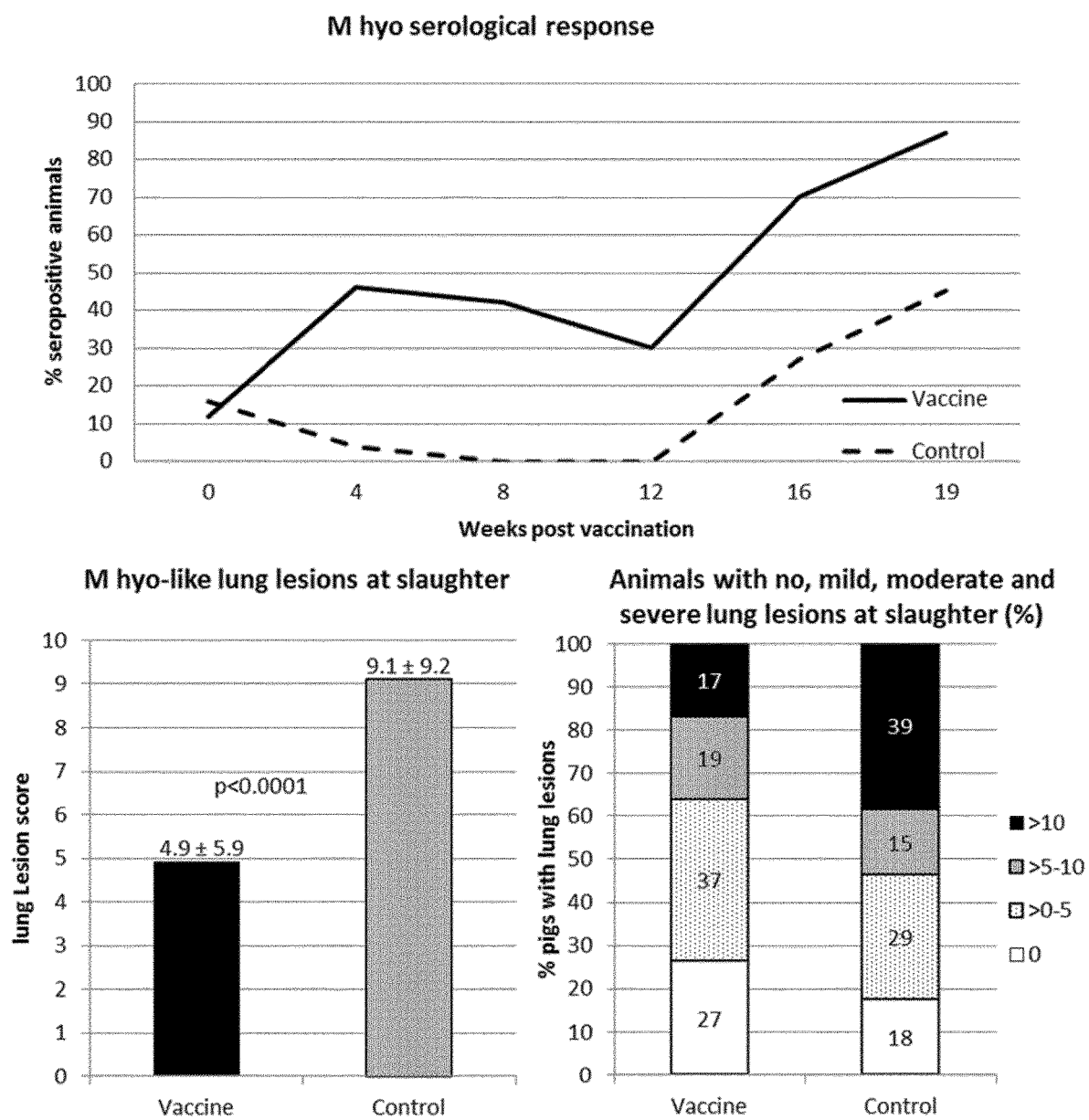

As shown in FIG. 4, 46% of vaccinated animals became M. hyo seropositive at 4 wpv. M. hyo seropositive control animals were observed at 16 wpv. At slaughter, the lung lesion scores in the vaccinated group were 46% lower than in the control animals (p<0.0001). In particular, the percentage of animals with severe lung lesions (score >10) was reduced by 56%. The number of animals with pleurisy was lower in the vaccinated group (32% versus 39%), but this reduction was not statistically significant (p=0.121).

Further, vaccination with Porcilis® PCV M Hyo induced a 34 g higher ADWG during fattening (p<0.0001) and a 19 g higher ADWG during the entire study period (p=0.0019) than in the control animals (Table 3). Although morbidity and mortality were both lower in the vaccinated group, the differences with the controls were not statistically significant.

5.3. Discussion

The present study supports that the new Porcilis® PCV M Hyo vaccine can safely be administered to piglets of 3 weeks of age. The frequency of systemic reactions was very low and as these reactions were also observed in the control group that was injected with saline, they appear to be more related to the treatment as such (the injection of a 2 ml volume) than a result of vaccination. Vaccination also did not have a negative effect on the growth of the pigs during the nursery phase and the local reactions were small and transient. An average increase in the rectal temperature of approximately 1° C. was observed at 4 hours post vaccination. However, as the temperature returned to normal the following day and as furthermore neither the general behaviour nor the feed intake (as measured by body weight at 3 or 7 weeks post vaccination in the field studies) of the animals was affected, this transient increase of rectal temperature is an acceptable vaccine related finding. Also, such an average increase of 1° C. is well within the limit of 1.5° C. that is allowed according to European Pharmacopoeia monograph 2448 (Porcine enzootic pneumonia vaccine (inactivated)).

The experimental challenge studies indicate that the onset of immunity occurs as early as 2 weeks (PCV2) to 4 weeks (M. hyo) post vaccination and lasts for at least 21 (M. hyo) to 22 (PCV2) weeks. This was demonstrated by a significant reduction of the PCV2 viral load in lymphoid organs and lungs and a significant reduction of M. hyo specific lung lesions. Accordingly, a single vaccination of animals at 3 weeks of age can protect fattening pigs against PCV2 and M. hyo infections during the fattening period.

The observations made during the challenge experiments were confirmed in the field efficacy trial: strong reductions in PCV2 viral load and M. hyo-induced lung lesions were measured. The field efficacy study showed that vaccination with Porcilis® PCV M Hyo not only reduced the level of the viral load of the pigs in serum but also shortened the time that virus was excreted via the nasal and faecal route after infection. The PCV2 infection encountered in the field study was primarily subclinical, but coughing as a sign of M. hyo infection was observed in the herd.

The serological and virological profiling of the animals in the field efficacy study indicates that PCV2 infection started at approximately 8 wpv and an increase in the number of M. hyo seroresponding animals was observed between 12-16 wpv. Considering that seroconversion against M. hyo generally occurs approximately 3-4 weeks post infection, the serological profile is indicative for an M. hyo infection at around the same time as the peak of the PCV2 infection (12-16 wpv, corresponding to 15 to 19 weeks of age). In case of dual infection with PCV2 and M. hyo, PCV2 has been shown to potentiate the severity of M. hyo lesions and M. hyo has been shown to potentiate the severity of PCV2 vireamia. And vaccination against one of the two pathogens alone is not sufficient to protect animals from dual infections with both pathogens. Therefore the effects of co-infections on the animal performance are usually more dramatic than with any of the two pathogens alone. The advantage of a combined PCV2-*M. hyo* vaccine, protecting against these synergistic disease effects, was reflected in the field study by a 34 g higher ADWG during the fattening period (time period between 10 and 22 weeks of age).

5.4. Conclusions:

Safety:

Vaccination resulted in a moderate temperature increase on the day of vaccination and mild systemic and local reactions in a low percentage of the vaccinated pigs.

Local reactions observed were small (max. 2 cm) and transient (max. 1 day).

Efficacy:

In short term (onset of immunity) and long term (duration of immunity) challenge studies with the individual pathogens, the PCV2/*M. hyo* combination vaccine significantly reduced the PCV2 load in serum, lymphoid tissue and lungs, as well as *M. hyo* induced lung lesions.

In a placebo-controlled field trial on a farm where both PCV2 and *M. hyo* were present, vaccination of piglets at 3 weeks of age resulted in a reduction of PCV2 vireamia and shedding, and lower lung lesion scores at slaughter Also, a positive effect from vaccination on the average daily weight gain (+34 g/day) in the fattening period was observed 5.5. Tables:

TABLE 2

Analysis of the safety of the PCV2/M.hyo combination vaccine

| | | Vaccine | Control | p-values |
|---|---|---|---|---|
| GLP safety study | number of pigs (n) | 12 | 12 | |
| | pigs with local reactions (%) | 0 | 0 | 1.000 |
| | pigs with macroscopic visible local reactions at necropsy (%) | 0 | 0 | 1.000 |
| | pigs with a systemic reaction (%) | 0 | 0 | 1.000 |
| | rectal temperature at 4 hours post vaccination (° C.) | 40.5 ± 0.4 | 39.4 ± 0.2 | <0.001 |
| Field safety study | number of pigs (n) | 84 | 85 | |
| | pigs with local reactions (%) | 13.1 | 3.5 | 0.0276 |
| | pigs with a systemic reaction (%) | 6.0 | 4.7 | 0.7464 |
| | rectal temperature at 4 hours post vaccination (° C.) | 40.6 ± 0.6 | 39.5 ± 0.4 | <0.0001 |
| | average daily weight gain (g/day) during the observation period (3-6 wk of age) | 245 ± 8 | 248 ± 8 | 0.7053 |
| Field safety and efficacy study | number of pigs (n) | 302 | 303 | |
| | pigs with local reactions (%) | 1.3 | 0.7 | 0.4504 |
| | pigs with a systemic reaction (%) | 2.6 | 0.7 | 0.0630 |
| | average daily weight gain (g/day) during nursery (3-10 wk of age) | 360 ± 4 | 369 ± 5 | 0.0839 |

TABLE 3

Descriptive data of experimental animals and their performance in the field efficacy trial with the PCV2/M.hyo combination vaccine.

| | Age (weeks) | Vaccine | Control | Diff[1] | p-value |
|---|---|---|---|---|---|
| number of pigs (n) | study inclusion | 302 | 303 | | |
| number of males/females (n) | | 155/147 | 160/143 | | |
| Age (days) | | 17.9 | 17.9 | | |
| morbidity (%) | 3-22 | 2.6 | 3.3 | −0.7 | 0.6373 |
| mortality (%) | 3-10 | 1.3 | 1.3 | 0.0 | 0.9960 |
| | 10-22 | 2.7 | 3.7 | −1.0 | 0.4890 |
| | 3-22 | 3.6 | 5.0 | −1.4 | 0.5563 |
| ADWG (g/day) | 3-10 | 360 ± 4 | 369 ± 4 | −9 | 0.0839 |
| | 10-22 | 757 ± 7 | 723 ± 7 | +34 | <0.0001 |
| | 3-22 | 612 ± 5 | 593 ± 5 | +19 | 0.0019 |

[1]Vaccine group minus Control group

6. Effect of conditions for binding *M. hyo* antigen to Aluminium-hydroxide adjuvant 6.1. Introduction In a further study the conditions of the binding of *M. hyo* antigen to Aluminium-hydroxide adjuvant were varied to test their effect on the efficiency of the forming of the antigen/adjuvant complex.

Specifically the influence of the temperature, pH and amount of Aluminium-hydroxide on the binding of *M. hyo* antigen was investigated by preparing a number of complete o/w vaccine formulations, at small scale. Next, the relative amount of the *M. hyo* antigen that was bound in the antigen/adjuvant complex was determined, both in the complete vaccine emulsion, and in samples of pellet or supernatant after centrifugation of the vaccine emulsion.

6.2. Materials and Methods 6.2.1. Vaccine Emulsion Preparation

The preparation of the different vaccine formulations was essentially as described in Example 3. From standard batches of *M. hyo* or PCV2 antigen, *M. hyo* antigen was added to a concentration of 6% (w/v) and PCV2 antigen was added to a final concentration of 2500 U/ml. Vaccine emulsions of 20 ml were prepared under different conditions, see Table 4. After preparation, all vaccines were stored at 2-8° C. until testing.

TABLE 4

Variation in parameters for the different vaccines

| No. | Temperature during adsorption | pH during adsorption | Amount of Aluminium-hydroxide (w/w) |
|---|---|---|---|
| 1 | ambient temperature (20-25° C.) | no adjustment (pH 7.0-7.3) | 9.8% |
| 2 | 4° C. | | |
| 3 | 30° C. | | |
| 4 | ambient temperature | 6.0 | |
| 5 | | 8.0 | |
| 6 | | no adjustment | 5% |
| 7 | | | 25% |

6.2.2. Sample Preparation

Ten ml of a vaccine was centrifuged at low g value (20 minutes at 600×g), and supernatant (8.5 ml) was removed. From sample no. 7 only 7.5 ml supernatant could be removed because the pellet had a larger volume due to the higher amount of Aluminium-hydroxide. Pellets were supplemented and homogenized with a volume of 0.9% physiological salt, that was equal to the volume of the supernatant that had been removed, to be able to compare same volumes of 'pellet' and supernatant.

6.2.3. *M. Hyo* Antigen Quantification

The amount of *M. hyo* antigen in a test sample could be measured with a standard Elisa, both for the supernatant as for the pellet samples. Calculation of antigen amount from OD's measured was done with a computer program. Each sample was tested twice and vaccine, pellet and supernatant of an individual blend were tested simultaneously on one microtiter plate. Results presented in Table 5 are the average values of each duplo. The relative potency unit (RPU) value of a pellet and a supernatant were calculated relative to the amount of *M. hyo* antigen in their respective complete vaccine emulsion, which was set at 100%.

6.3. Results

Centrifugation of samples was done at low g value; this was enough to pellet the Aluminium-hydroxide, without pelletting the *M. hyo* antigen independent of its binding to the adjuvant. Also at these low g values the supernatant still consisted of an oil-in-water emulsion.

To verify that the centrifugation was not to hard, a control sample was prepared by direct mixing of *M. hyo* and PCV2 antigens with an empty Emunade o/w emulsion, followed by immediate centrifugation at the same low g value. The results of these control samples demonstrate that under these conditions *M. hyo* antigen as such was not precipitated to a significant level: the 13% *M. hyo* antigen detected in this pellet, merely represents the volume part of pellet from the total volume of this vaccine tested (1.5 ml from 10 ml).

Except for the samples with deviation in pH values or temperature of incubation, other samples had a pH at between 6.8 and 7.3, and ambient temperature at the time of the experiment was 22° C.

Standard conditions were: 0/N incubation, at ambient temperature, at pH between 6.5 and 7.5, and with 9.8 w/w % Aluminium-hydroxide adjuvant.

The percentages RPU of *M. hyo* antigen measured in the pellet and supernatant of the various samples are depicted in Table 5. For temperature and pH, no significant influence was observed on the binding of *M. hyo* antigen to the Aluminium-hydroxide adjuvant. The relative amount of *M. hyo* antigen detected in the Aluminium-hydroxide phase was between 74-82% for these conditions.

However the amount of Aluminium-hydroxide in the emulsion did have a significant impact: a reduction from 9.8 to 5% w/w, almost halved the relative amount of *M. hyo* antigen in the pellet (48%), while an increase in Aluminium-hydroxide amount to 25% showed an almost complete binding of the *M. hyo* antigen (96%).

TABLE 5

Relative percentages of M.hyo antigen present in pellet and supernatant

| no. | condition | value | M.hyo antigen in average RPU/ml, as % of value in corresp. vaccine | |
| --- | --- | --- | --- | --- |
| | | | pellet | sup |
| 1 | standard | | 74% | 26% |
| 2 | incubation temperature @ | 4° C. | 81% | 19% |
| 3 | adsorbtion | 30° C. | 82% | 18% |
| 4 | pH value @ | pH = 6 | 80% | 20% |
| 5 | adsorbtion | pH = 8 | 75% | 25% |

TABLE 5-continued

Relative percentages of M.hyo antigen present in pellet and supernatant

| no. | condition | value | M.hyo antigen in average RPU/ml, as % of value in corresp. vaccine | |
| --- | --- | --- | --- | --- |
| | | | pellet | sup |
| 6 | amount of Aluminium- | 5% | 48% | 52% |
| 7 | hydroxide | 25% | 96% | 4% |
| Control | direct mix & centrifugation | | 13% | 87% |

6.4. Conclusion

No significant difference was found with regard to binding of *M. hyo* antigen to Aluminium-hydroxide with variation in temperature or pH conditions of the binding. An effect was found of the variation in Aluminium-hydroxide amount at binding.

LEGEND TO THE FIGURES

FIG. 1: Results of PCV2 challenge studies:
Onset- and duration of immunity, expressed in anti-PCV2 antibody titre, and in PCV2 viral load, as detected by qPCR.

FIG. 2: Results of *M. hyo* challenge studies:
Onset- and duration of immunity, expressed in anti-*M. hyo* antibody titre, and in lung lesion score.

Figure 3:
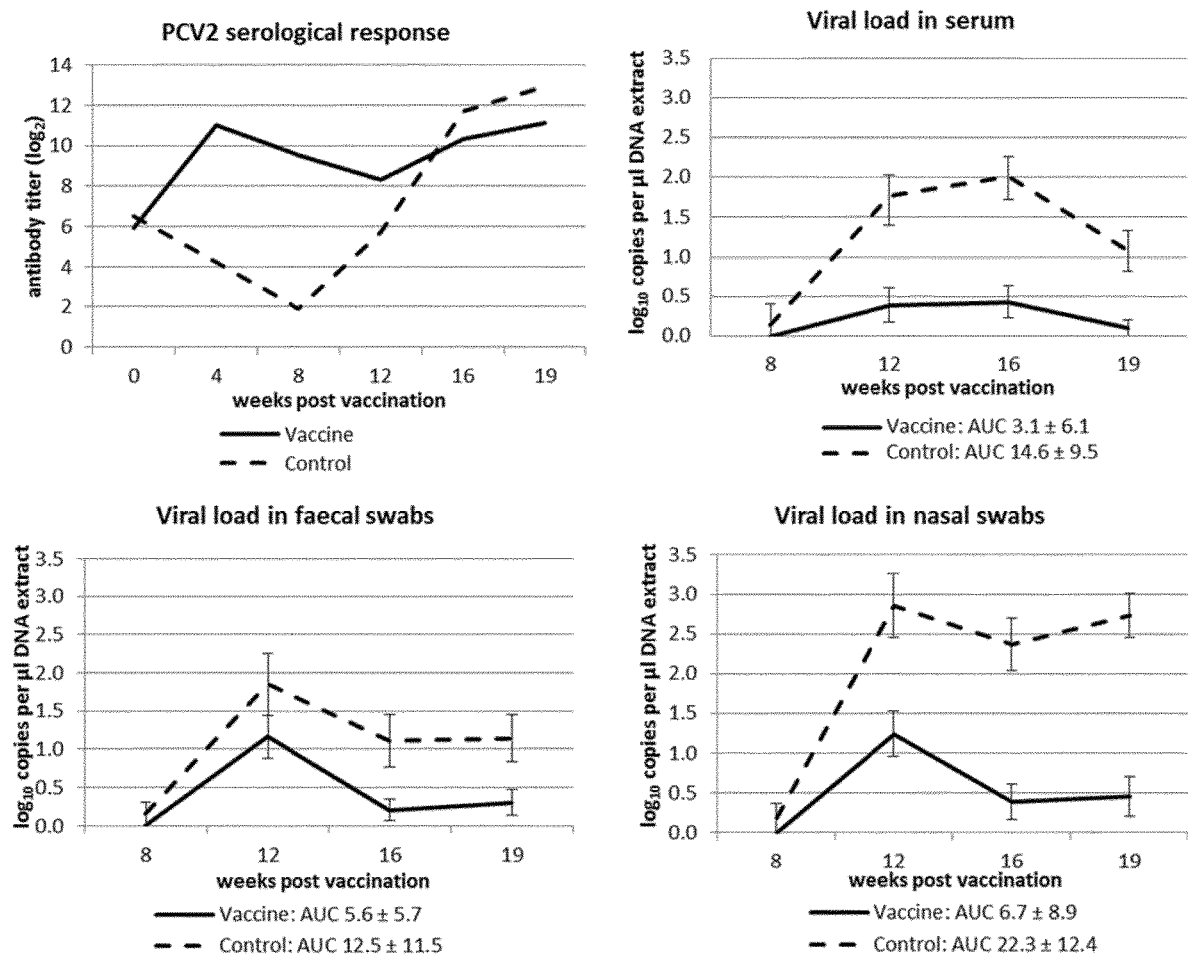

FIG. 3: PCV2 data from a field efficacy study:
Results from a field efficacy study wherein a PCV2 field-infection was encountered between weeks 8 and 12 of the experiment. Results are presented from serology and viral DNA detection.

FIG. 4: *M. hyo* data from a field efficacy study:
Results from a field efficacy study wherein an *M. hyo* field-infection was encountered around week 12 of the experiment. Results are presented from serology and lung lesion scores.

The invention claimed is:

1. A process for preparing an antigen composition for a ready-to-use combination vaccine for swine, wherein the antigen composition comprises a *Mycoplasma hyopneumoniae* (*M. hyo*) antigen and a porcine circovirus type 2 (PCV2) antigen;
   wherein the process comprises a step of admixing the PCV2 antigen to a pre-formed antigen/adjuvant complex of the *M. hyo* antigen adsorbed to an Aluminium-hydroxide adjuvant to form the antigen mixture;
   wherein the pre-formed antigen/adjuvant complex is obtained by the steps of:
   a) admixing the Aluminium-hydroxide adjuvant and the *M. hyo* antigen, in a watery carrier at a pH at which the Aluminium-hydroxide adjuvant is positively charged to form a mixture; and
   b) incubating said mixture to allow the adsorption of the *M. hyo* antigen to the Aluminium-hydroxide adjuvant to form an antigen/adjuvant complex.

2. The process of claim 1, wherein the *M. hyo* antigen is an *M. hyo* bacterin.

3. A process for preparing a vaccine comprising a step of admixing the antigen composition of claim 1, and an additional adjuvant.

4. A process for preparing a vaccine, comprising a step of emulsifying the antigen composition of claim 1, and a mineral oil, into an oil-in-water emulsion.

5. The process of claim 1, wherein the PCV2 antigen is encoded by a PCV2 ORF2 coding sequence.

6. The process of claim 5, wherein the PCV2 ORF2 antigen is a virus-like particle.

7. The process of claim 2, wherein the PCV2 antigen is encoded by a PCV2 ORF2 coding sequence.

8. The process of claim 1, wherein the watery carrier is a balanced salt solution.

9. The process of claim 8, wherein the pH of the watery carrier is between 6 and 8.

10. The process of claim 1, wherein said mixture is essentially free of other components.

11. The process of claim 1, wherein said incubating is performed for 10-20 hours at room temperature.

12. The process of claim 11, wherein said incubating comprises a gentle agitation of the said mixture.

13. An antigen composition obtained by a process according to claim 1.

14. The antigen composition according to claim 13, characterised in that at least 50% of the *M. hyo* antigen is located in the antigen/adjuvant complex.

15. The antigen composition according to claim 14, characterised in that at least 50% of the protein binding capacity of the Aluminium-hydroxide adjuvant is used by the *M. hyo* antigen.

16. A ready-to-use vaccine for swine, for preventing or reducing infection by *M. hyo* or PCV2 and associated signs of disease, the vaccine comprising the antigen composition obtained by a process according to claim 1, and an additional adjuvant.

17. The vaccine according to claim 16, characterised in that the vaccine is an oil-in-water emulsion and the additional adjuvant is a mineral oil.

18. A vaccine according to claim 16, characterised in that the vaccine comprises additional antigenic material that is derived from a micro-organism pathogenic to swine.

19. The antigen composition obtained by a process according to claim 1, for use in a vaccine for swine for preventing or reducing infection by *M. hyo* or PCV2 and associated signs of disease.

20. A method for preventing or reducing infection by *M. hyo* or PCV2 in swine and associated signs of disease, the method comprising the administration of the vaccine according to claim 16, to swine.

* * * * *

UNITED STATES PATENT AND TRADEMARK OFFICE
CERTIFICATE OF CORRECTION

| | |
|---|---|
| PATENT NO. | : 10,568,954 B2 |
| APPLICATION NO. | : 15/534232 |
| DATED | : February 25, 2020 |
| INVENTOR(S) | : Maarten Hendrick Witvliet, Theo Jansen and Huchappa Jayappa |

Page 1 of 1

It is certified that error appears in the above-identified patent and that said Letters Patent is hereby corrected as shown below:

On the Title Page

Column 1, item (54), and In the Specification, Column 1, Line 1:
Title: PROCESS FOR READY-TO-USE PCV/M.HYO COMBINATION VACCINE
Should read: PROCESS FOR READY-TO-USE PCV2/M.HYO COMBINATION VACCINE Signed and Sealed this
Sixth Day of December, 2022

Katherine Kelly Vidal
*Director of the United States Patent and Trademark Office*